US012793408B1

(12) United States Patent
Skole et al.

(10) Patent No.: US 12,793,408 B1

(45) Date of Patent: Nov. 10, 2026

(54) FOREST MAPPING AND CARBON ESTIMATION SYSTEM AND METHOD FOR OPERATING THE SAME

(71) Applicant: Board of Trustees of Michigan State University, East Lansing, MI (US)

(72) Inventors: David Skole, Okemos, MI (US); Jay Samek, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 19/230,538

(22) Filed: Jun. 6, 2025

(51) Int. Cl.

| | |
|---|---|
| ***G06V 20/13*** | (2022.01) |
| ***G01N 33/00*** | (2006.01) |
| ***G06V 10/26*** | (2022.01) |
| ***G06V 10/764*** | (2022.01) |
| ***G06V 20/10*** | (2022.01) |

(52) U.S. Cl.
CPC ......... *G06V 20/13* (2022.01); *G01N 33/0098* (2013.01); *G06V 10/273* (2022.01); *G06V 10/764* (2022.01); *G06V 20/188* (2022.01)

(58) Field of Classification Search
CPC .... G06V 10/273; G06V 10/764; G06V 20/13; G06V 20/188
See application file for complete search history.

(56) References Cited

PUBLICATIONS

Tucker, Compton, et al. "Sub-continental-scale carbon stocks of individual trees in African drylands." Nature 615.7950 (2023): 80-86. (Year: 2023).*

Manrique, Silvina M., Virgilio Núñez, and Judith Franco. "Estimating aboveground biomass in native forest using remote sensing data combined with spectral radiometry." GeoFocus. International Review of Geographical Information Science and Technology 12 (2012): 349-373. (Year: 2012).*

Lutz, J.A.; Furniss, T.J.; Johnson, D.J.; Davies, S.J.; Allen, D.; Alonso, A.; Anderson-Teixeira, K.J.; Andrade, A.; Baltzer, J.; Becker, K.M.; et al. Global importance of large-diameter trees. Glob. Ecol. Biogeogr. 2018, 27, 849-864.

Ali, A.; Lin, S.L.; He, J.K.; Kong, FM.; Yu, J.H.; Jiang, H.S. Big-sized trees overrule remaining trees' attributes and species richness as determinants of aboveground biomass in tropical forests. Glob. Chang. Biol. 2019, 25, 2810-2824.

Latifi, H.; Heurich, M. Multi-scale remote sensing-assisted forest inventory: A glimpse of the state-of-the-art and future prospects. Remote Sens. 2019, 11, 1260.

(Continued)

*Primary Examiner* — Tracy Mangialaschi

(74) *Attorney, Agent, or Firm* — Harness, Dickey & Pierce, P.L.C.

(57) ABSTRACT

A method and system for generating a carbon map includes receiving at a satellite, reflected light from an object, forming high resolution satellite image data at the satellite, communicating the high resolution satellite image data to a pre-processing system, pre-processing the high resolution satellite image data to form pre-processed data, communicating the pre-processed data to a trained classifier, determining at the trained classifier a crown projected area for individual trees, determining a carbon stock for each of the individual trees at a processing system and determining a carbon map for the individual trees.

12 Claims, 17 Drawing Sheets

(56) References Cited

PUBLICATIONS

Almeida, D.R.A.D .; Stark, S.C.; Chazdon, R.; Nelson, B.W.; César, R.G.; Meli, P.; Gorgens, E.B.; Duarte, M.M.; Valbuena, R.; Moreno, V.S.; et al. The effectiveness of lidar remote sensing for monitoring forest cover attributes and landscape restoration. For. Ecol. Manag. 2019, 438, 34-43.
Muller-Landau, H.C.; Condit, R.S.; Chave, J.; Thomas, S.C.; Bohlman, S.A.; Bunyavejchewin, S.; Davies, S.; Foster, R.; Gunatilleke, S.; Gunatilleke, N.; et al. Testing metabolic ecology theory for allometric scaling of tree size, growth and mortality in tropical forests. Ecol. Lett. 2006, 9, 575-588.
Jucker, T.; Caspersen, J.; Chave, J.; Antin, C.; Barbier, N.; Bongers, F.; Dalponte, M.; van Ewijk, K.Y.; Forrester, D.I.; Haeni, M.; et al. Allometric equations for integrating remote sensing imagery into forest monitoring programmes. Glob. Chang. Biol. 2017, 23, 177-190.
Hemery, G.E.; Savill, P.S.; Pryor, S.N. Applications of the crown diameter-stem diameter relationship for different species of broadleaved trees. For. Ecol. Manag. 2005, 215, 285-294.
Loubota Panzou, G.J.; Fayolle, A.; Jucker, T.; Phillips, O.L.; Bohlman, S.; Banin, L.F.; Lewis, S.L.; Affum-Baffoe, K.; Alves, L.F.; Antin, C.; et al. Pantropical variability in tree crown allometry. Glob. Ecol. Biogeogr. 2021, 30, 459-475.
Baccini, A.; Laporte, N.; Goetz, S.J.; Sun, M.; Dong, H. A first map of tropical Africa's above-ground biomass derived from satellite imagery. Environ. Res. Lett. 2008, 3, 045011. Forests 2021, 12, 1652 25 of 25.
Baccini, A.G.S.J.; Goetz, S.J.; Walker, W.S.; Laporte, N.T.; Sun, M.; Sulla-Menashe, D.; Hackler, J.; Beck, P.S.A.; Dubayah, R.; Friedl, M.A.; et al. Estimated carbon dioxide emissions from tropical deforestation improved by carbon-density maps. Nat. Clim. Chang. 2012, 2, 182-185.
Saatchi, S.S.; Harris, N.L.; Brown, S.; Lefsky, M.; Mitchard, E.T.; Salas, W.; Zutta, B.R.; Buermann, W.; Lewis, S.L.; Hagen, S.; et al. Benchmark map of forest carbon stocks in tropical regions across three continents. Proc. Natl. Acad. Sci. USA 2011, 108, 9899-9904.
Spawn, S.A.; Sullivan, C.C.; Lark, T.J.; Gibbs, H.K. Harmonized global maps of above and belowground biomass carbon density in the year 2010. Sci. Data 2020, 7, 112.
Skole, D.L.; Mbow, C.; Mugabowindekwe, M.; Brandt, M.S.; Samek, J.H. Trees outside of forests as natural climate solutions. Nat. Clim. Chang. 2021, 11.
Verdone, M.; Seidl, A. Time, space, place, and the Bonn Challenge global forest restoration target. Restor. Ecol. 2017, 25, 903-911.
Stanturf, J.A.; Kleine, M.; Mansourian, S.; Parrotta, J.; Madsen, P.; Kant, P.; Burns, J.; Bolte, A. Implementing forest landscape restoration under the Bonn Challenge: A systematic approach. Ann. For. Sci. 2019, 76, 50.
Guariguata, M.R.; Evans, K. A diagnostic for collaborative monitoring in forest landscape restoration. Restor. Ecol. 2020, 28, 742-749.
Mansourian, S.; Dudley, N.; Vallauri, D. Forest landscape restoration: Progress in the last decade and remaining challenges. Ecol. Restor. 2017, 35, 281-288.
Schleussner, C.F., Lissner, T.K., Fischer, E.M., Wohland, J., Perrette, M., Golly, A., Rogelj, J., Childers, K., Schewe, J., Frieler, K. and Mengel, M., 2016. Differential climate impacts for policy-relevant limits to global warming: The case of 1.5 deg. C and 2 deg. C. Earth system dynamics, 7(2), pp. 327-351.
Sanderson, B.M., Xu, Y., Tebaldi, C, Wehner, M., O'Neill, B., Jahn, A., Pendergrass, A.G., Lehner, F, Strand, W.G., Lin, L. and Knutti, R., 2017. Community climate simulations to assess avoided impacts in 1.5° C and 2° C futures. Earth System Dynamics, 8(3), pp. 827-847.
Mitchell, D., AchutaRao, K., Allen, M., Bethke, I., Beyerle, U., Ciavarella, A., Forster, P. M., Fuglestvedt, J., Gillett, N., Haustein, K. and Ingram, W., 2017. Half a degree additional warming, prognosis and projected impacts (HAPPI): background and experimental design. Geoscientific Model Development, 10(2), pp. 571-583.
Rogelj, J., Schleussner, C.F. and Hare, W., 2017. Getting it right matters: temperature goal interpretations in geoscience research. Geophysical Research Letters, 44(20), pp. 10-662.
Manabe, S., Stouffer, R.J., Spelman, M.J. and Bryan, K., 1991. Transient responses of a coupled ocean-atmosphere model to gradual changes of atmospheric CO2. Part I. Annual mean response. Journal of Climate, 4(8), pp. 785-818.
Rugenstein, M., Bloch-Johnson, J., Abe-Ouchi, A., Andrews, T., Beyerle, U., Cao, L., Chadha, T., Danabasoglu, G., Dufresne, J.L., Duan, L. and Foujols, M.A., 2019. LongRunMIP: motivation and design for a large collection of millennial-length AOGCM simulations. Bulletin of the American Meteorological Society, 100(12), pp. 2551-2570.
Rugenstein, M., Bloch-Johnson, J., Gregory, J., Andrews, T., Mauritsen, T., Li, C., Frolicher, T.L., Paynter, D., Danabasoglu, G., Yang, S. and Dufresne, J.L., 2020. Equilibrium climate sensitivity estimated by equilibrating climate models. Geophysical Research Letters, 47(4), p.e2019GL083898.
King, A.D., Lane, T.P., Henley, B.J. and Brown, J.R., 2020. Global and regional impacts differ between transient and equilibrium warmer worlds. Nature Climate Change, 10(1), pp. 42-47.
Sigmond, M., Fyfe, J.C., Saenko, O.A. and Swart, N.C., 2020. Ongoing AMOC and related sea-level and temperature changes after achieving the Paris targets. Nature Climate Change, 10(7), pp. 672-677.
Sniderman, J.K., Brown, J.R., Woodhead, J.D., King, A.D., Gillett, N.P., Tokarska, K.B., Lorbacher, K., Hellstrom, J., Drysdale, R.N. and Meinshausen, M., 2019. Southern Hemisphere subtropical drying as a transient response to warming. Nature Climate Change, 9(3), pp. 232-236.
Hawkins, E. and Sutton, R., 2009. The potential to narrow uncertainty in regional climate predictions. Bulletin of the American Meteorological Society, 90(8), pp. 1095-1108.
Jones, C.D., Frölicher, T.L., Koven, C., MacDougall, A.H., Matthews, H.D., Zickfeld, K., Rogelj, J., Tokarska, K.B., Gillett, N.P., Ilyina, T. and Meinshausen, M., 2019. The Zero Emissions Commitment Model Intercomparison Project (ZECMIP) contribution to C4MIP: quantifying committed climate changes following zero carbon emissions. Geoscientific Model Development, 12(10), pp. 4375-4385.
Callahan, CW., Chen, C, Rugenstein, M., Bloch-Johnson, J., Yang, S. and Moyer, E.J., 2021. Robust decrease in El Niño/Southern Oscillation amplitude under long-term warming. Nature Climate Change, 11(9), pp. 752-757.
Mohtadi, M., Prange, M. and Steinke, S., 2016. Palaeoclimatic insights into forcing and response of monsoon rainfall. Nature, 533(7602), pp. 191-199.
Macdougall, A.H., Frölicher, T.L., Jones, CD., Rogelj, J., Matthews, H.D., Zickfeld, K., Arora, V.K., Barrett, N.J., Brovkin, V., Burger, FA. and Eby, M., 2020. Is there warming in the pipeline? A multi-model analysis of the Zero Emissions Commitment from CO2. Biogeosciences, 17(11), pp. 2987-3016.
Chao, S., 2012. Forest peoples: Nos. across the world (vol. 10, p. 2017). Moreton-in-Marsh, UK: Forest Peoples Programme.
Akinyemi, F.O., Ghazaryan, G. and Dubovyk, O., 2021. Assessing UN indicators of land degradation neutrality and proportion of degraded land for Botswana using remote sensing based national level metrics. Land degradation & development, 32(1), pp. 158-172.
Chomba, S., Sinclair, F, Savadogo, P., Bourne, M. and Lohbeck, M., 2020. Opportunities and constraints for using farmer managed natural regeneration for land restoration in sub-Saharan Africa. "Frontiers in Forests and Global Change," 3, p. 571679.
Griscom, B.W., Adams, J., Ellis, p. W., Houghton, R.A., Lomax, G., Miteva, D.A., Schlesinger, W.H., Shoch, D., Siikamaki, J.V., Smith, p. and Woodbury, P., 2017. Natural climate solutions. "Proceedings of the National Academy of Sciences," 114(44), pp. 11645-11650.
Lohbeck, M., Albers, P., Boels, L.E., Bongers, F, Morel, S., Sinclair, F, Takoutsing, B., VÃ¥gen, T.G., Winowiecki, L. A. and Smith-

(56) References Cited

PUBLICATIONS

Dumont, E., 2020. Drivers of farmer-managed natural regeneration in the Sahel. Lessons for restoration. "Scientific reports," 10(1), p. 15038.
Report of the Conference of the Parties serving as the meeting of the Parties to the Paris Agreement on its third session, held in Glasgow from 1 Novemer to Nov. 12, 2021. In "Framework Convention on Climate Change, United Nations.".
Zarin, D.J., Harris, N.L., Baccini, A., Aksenov, D., Hansen, M.C, Azevedoâ€Ramos, C, Azevedo, T., Margono, B.A., Alencar, A.C, Gabris, C and Allegretti, A., 2016. Can carbon emissions from tropical deforestation drop by 50% in 5 years ?. Global change biology, 22(4), pp. 1336-1347.
Mbow, C., Toensmeier, E., Brandt, M., Skole, D., Dieng, M., Garrity, D. and Poulter, B., 2020. Agroforestry as a solution for multiple climate change challenges in Africa. In Climate change and agriculture (pp. 339-374). Burleigh Dodds Science Publishing.
Bousias Alexakis, E. and Armenakis, C, 2020. Evaluation of UNet and UNet++ architectures in high resolution image change detection applications. The International Archives of the Photogrammetry, Remote Sensing and Spatial Information Sciences, 43, pp. 1507-1514.
Brandt, J., Ertel, J., Spore, J. and Stolle, F., 2023. Wall-to-wall mapping of tree extent in the tropics with Sentinel-1 and Sentinel-2. Remote Sensing of Environment, 292, p. 113574.
Koonce, B. 2021. ResNet 50. Convolutional neural networks with swift for tensorflow: image recognition and dataset categorization, Apress, Spinger Science and Business Media, New York, 245pp.
Mascarenhas, S. and Agarwal, M., Nov. 2021, A comparison between VGG16, VGG19 and ResNet50 architecture frameworks for Image Classification. In 2021 International conference on disruptive technologies for multi-disciplinary research and applications (CENTCON) (vol. 1, pp. 96-99). IEEE.
Sushma, L. and Lakshmi, K.P., 2020. An analysis of convolution neural network for image classification using different models. Int J Eng Res Technol (IJERT), 9(10).
Seneviratne, S.I., Donat, M.G., Pitman, A.J., Knutti, R. and Wilby, R.L., 2016. Allowable CO2 emissions based on regional and impact-related climate targets. Nature, 529(7587), pp. 477-483.
Tebaldi, C. and Knutti, R., 2018. Evaluating the accuracy of climate change pattern emulation for low warming targets. Environmental Research Letters, 13(5), p. 055006.
Hansen, M.C.; Potapov, P.V.; Moore, R.; Hancher, M.; Turubanova, S.A.; Tyukavina, A.; Thau, D.; Stehman, S.V.; Goetz, S.J.; Loveland, T.R.; et al. High-resolution global maps of 21st-century forest cover change. Science 2013, 342, 850-853.
Fischer, R.; Taubert, F.; Muller, M.S.; Groeneveld, J.; Lehmann, S.; Wiegand, T.; Huth, A. Accelerated forest fragmentation leads to critical increase in tropical forest edge area. Sci. Adv. 2021, 7, 7012.
Vancutsem, C.; Achard, F.; Pekel, J.F.; Vieilledent, G.; Carboni, S.; Simonetti, D.; Gallego, J.; Aragao, L.E.; Nasi, R. Long-term (1990-2019) monitoring of forest cover changes in the humid tropics. Sci. Adv. 2021, 7, 1603.
Miller, D.C.; Muñoz-Mora, J.C.; Christiaensen, L. Prevalence, economic contribution, and determinants of trees on farms across Sub-Saharan Africa. Forest Policy Econ. 2017, 84, 47-61. Forests 2021, 12, 1652 23 of 25.
Zomer, R.J.; Neufeldt, H.; Xu, J .; Ahrends, A.; Bossio, D.; Trabucco, A.; Van Noordwijk, M.; Wang, M. Global Tree Cover and Biomass Carbon on Agricultural Land: The contribution of agroforestry to global and national carbon budgets. Sci. Rep.and Biomass Carbon on Agricultural Land: The contribution of agroforestry to global and national carbon budgets. Sci. Rep. 2016, 6, 29987.
Schnell, S.; Altrell, D.; Ståhl, G.; Kleinn, C. The contribution of trees outside forests to national tree biomass and carbon stocks—a comparative study across three continents. Environ. Monit. Assess. 2015, 187, 4197.
Mbow, C.; Van Noordwijk, M.; Luedeling, E.; Neufeldt, H.; Minang, P.A.; Kowero, G. Agroforestry solutions to address food security and climate change challenges in Africa. Curr. Opin. Environ. Sustain. 2014, 6, 61-67.
Beckschäfer, P.; Schnell, S.; Kleinn, C. Monitoring and Assessment of Trees Outside Forests (TOF). In Agroforestry; Dagar, J.C, Tewari, V.P., Eds.; Springer Nature: Singapore, 2017; pp. 137-161.
Brandt, M.; Rasmussen, K.; Hiernaux, P.; Herrmann, S.; Tucker, C.J.; Tong, X.; Tian, F.; Mertz, O.; Kergoat, L.; Mbow, C.; et al. Reduction of tree cover in West African woodlands and promotion in semi-arid farmlands. Nat. Geosci. 2018, 11, 328-333.
Zomer, R.J.; Trabucco, A.; Coe, R.; Place, F. Trees on Farm: Analysis of Global Extent and Geographical Patterns of Agroforestry; ICRAF Working Paper-World Agroforestry Centre 89; World Agroforestry Centre: Nairobi, Kenya, 2009.
Mbow, C.; Smith, P.; Skole, D.; Duguma, L.; Bustamante, M. Achieving mitigation and adaptation to climate change through sustainable agroforestry practices in Africa. Curr. Opin. Environ. Sustain. 2014, 6, 8-14.
Verchot, L.V.; Van Noordwijk, M.; Kandji, S.; Tomich, T.; Ong, C.; Albrecht, A.; Mackensen, J.; Bantilan, C.; Anupama, K.V.; Palm, C. Climate change: Linking adaptation and mitigation through agroforestry. Mitig. Adapt. Strateg. Glob. Chang. 2007, 12, 901-918.
Dardel, C.; Kergoat, L.; Hiernaux, P.; Mougin, E.; Grippa, M.; Tucker, C.J. Re-greening Sahel: 30 years of remote sensing data and field observations (Mali, Niger). Remote Sens. Environ. 2014, 140, 350-364.
Sitch, S.; Friedlingstein, P.; Gruber, N.; Jones, S.D.; Murray-Tortarolo, G.; Ahlstrom, A.; Doney, S.C.; Graven, H.; Heinze, C.; Huntingford, C.; et al. Recent trends and drivers of regional sources and sinks of carbon dioxide. Biogeosciences 2015, 12, 653-679.
Brandt, M.; Mbow, C.; Diouf, A.A.; Verger, A.; Samimi, C.; Fensholt, R. Ground-and satellite-based evidence of the biophysical mechanisms behind the greening Sahel. Glob. Chang. Biol. 2015, 21, 1610-1620.
Mbow, C.; Brandt, M.; Ouedraogo, I.; De Leeuw, J.; Marshall, M. What four decades of earth observation tell US about land degradation in the Sahel? Remote Sens. 2015, 7, 4048-4067.
Brandt, M.; Rasmussen, K.; Peñuelas, J.; Tian, F.; Schurgers, G.; Verger, A.; Mertz, O.; Palmer, J.R.; Fensholt, R. Human population growth offsets climate-driven increase in woody vegetation in sub-Saharan Africa. Nat. Ecol. Evol. 2017, 1, 81.
Brandt, M.; Tappan, G.; Diouf, A.A.; Beye, G.; Mbow, C.; Fensholt, R.Woody vegetation die off and regeneration in response to rainfall variability in theWest African Sahel. Remote Sens. 2017, 9, 39.
Brandt, M.; Hiernaux, P.; Rasmussen, K.; Tucker, C.J.; Wigneron, J.P.; Diouf, A.A.; Herrmann, S.M.; Zhang, W.; Kergoat, L.; Mbow, C.; et al. Changes in rainfall distribution promote woody foliage production in the Sahel. Commun. Biol. 2019, 2, 133.
Zhang, W.; Brandt, M.; Guichard, F.; Tian, Q.; Fensholt, R. Using long-term daily satellite based rainfall data (1983-2015) to analyze spatio-temporal changes in the Sahelian rainfall regime. J. Hydrol. 2017, 550, 427-440.
Brandt, M.; Wigneron, J.P.; Chave, J.; Tagesson, T.; Penuelas, .; Ciais, P.; Rasmussen, K.; Tian, F.; Mbow, C.; Al-Yaari, A.; et al. Satellite passive microwaves reveal recent climate-induced carbon losses in African drylands. Nat. Ecol. Evol. 2018, 2, 827-835.
Brandt, M.; Tucker, C.J.; Kariryaa, A.; Rasmussen, K.; Abel, C.; Small, J.; Chave, J.; Rasmussen, L.V.; Hiernaux, P.; Diouf, A.A.; et al. An unexpectedly large count of trees in the West African Sahara and Sahel. Nature 2020, 587, 78-82.
Walker, S.M.; Pearson, T.R.H.; Casarim, F.M.; Harris, N.; Petrova, S.; Grais, A.; Swails, E.; Netzer, M.; Goslee, K.M.; Brown, S. Standard Operating Procedures for Terrestrial Carbon Measurement; Version Feb. 2018; Winrock International: Washington, DC, USA, 2012.
Dons, K.; Smith-Hall, C.; Meilby, H.; Fensholt, R. Operationalizing measurement of forest degradation: Identification and quantification of charcoal production in tropical dry forests using very high resolution satellite imagery. Int. J. Appl. Earth Obs. Geoinf. 2015, 39, 18-27.
Niang-Diop, F.; Christensen, S.N.; Barfod, A.S.; Sambou, B.; Diop, M.; Goudiaby, A.; Padonou, E.A.; Lykke, A.M. Trees on farmlands

(56) References Cited

PUBLICATIONS in the western central part of Senegal: Implications for a carbon project. Int. J. Biol. Chem. Sci. 2020, 14, 1294-1307.
Mbow, C.; Verstraete, M.M.; Sambou, B.; Diaw, A.T.; Neufeldt, H. Allometric models for aboveground biomass in dry savanna trees of the Sudan and Sudan-Guinean ecosystems of Southern Senegal. J. For. Res. 2014, 19, 340-347.
Rasmussen, M.O.; Göttsche, F.M.; Diop, D.; Mbow, C.; Olesen, F.S.; Fensholt, R.; Sandholt, I. Tree survey and allometric models for tiger bush in northern Senegal and comparison with tree parameters derived from high resolution satellite data. Int. J. Appl. Earth Obs. Geoinf. 2011, 13, 517-527.
Kuyah, S.; Dietz, J.; Muthuri, C.; Jamnadass, R.; Mwangi, P.; Coe, R.; Neufeldt, H. Allometric equations for estimating biomass in agricultural landscapes: II. Aboveground biomass. Agric. Ecosyst. Environ. 2012, 158, 216-224. Forests 2021, 12, 1652 24 of 25.
Brown, S. Estimating Biomass and Biomass Change of Tropical Forests: A Primer; Forestry Paper 134; Food and Agriculture Organization of the United Nations: Rome, Italy, 1997.
IPCC. Good Practice Guidance for Land Use, Land-Use Change and Forestry; Penman, J., Gytarsky, M., Hiraishi, T., Krug, T., Kruger, D., Pipatti, R., Buendia, L., Miwa, K., Ngara, T., Tanabe, K., et al., Eds.; IPCC National Greenhouse Gas Inventories Programme, Institute for Global Environmental Strategies: Hayama, Japan, 2003; 593p.
IPCC. 2006 IPCC Guidelines for National Greenhouse Gas Inventories; Eggleston, H.S., Buendia, L., Miwa, K., Ngara, T., Tanabe, K., Eds.; IPCC National Greenhouse Gas Inventories Programme, Institute for Global Environmental Strategies: Hayama, Japan, 2006.
Chabi, A.; Lautenbach, S.; Tondoh, J.E.; Orekan, V.O.A.; Adu-Bredu, S.; Kyei-Baffour, N.; Mama, V.J.; Fonweban, J. The relevance of using in situ carbon and nitrogen data and satellite images to assess aboveground carbon and nitrogen stocks for supporting national REDD+ programmes in Africa. Carbon Balance Manag. 2019, 14, 12.
Chave, J.; Réjou-Méchain, M.; Búrquez, A.; Chidumayo, E.; Colgan, M.S.; Delitti, W.B.; Duque, A.; Eid, T.; Fearnside, P.M.; Goodman, R.C.; et al. Improved allometric models to estimate the aboveground biomass of tropical trees. Glob. Chang. Biol. 2014, 20, 3177-3190.
Henry, M.; Picard, N.; Trotta, C.; Manlay, R.; Valentini, R.; Bernoux, M.; Saint-André, L. Estimating tree biomass of sub-Saharan African forests: A review of available allometric equations. Silva Fenn. 2011, 45, 477-569.
Balima, L.H.; Nacoulma, B.M.I.; Bayen, P.; Dimobe, K.; Kouame, F.N.G.; Thiombiano, A. Aboveground biomass allometric equations and distribution of carbon stocks of the African oak (Afzelia africana Sm.) in Burkina Faso. J. For. Res. 2020, 31, 1699-1711.
Ganamé, M.; Bayen, P.; Ouédraogo, I.; Balima, L.H.; Thiombiano, A. Allometric models for improving aboveground biomass estimates in West African savanna ecosystems. Trees For. People 2021, 4, 100077.
Sawadogo, L.; Savadogo, P.; Tiveau, D.; Dayamba, S.D.; Zida, D.; Nouvellet, Y.; Oden, P.C.; Guinko, S. Allometric prediction of above-ground biomass of eleven woody tree species in the Sudanian savanna-woodland of West Africa. J. For. Res. 2010, 21, 475-481.
Chabi, A.; Lautenbach, S.; Orekan, V.O.A.; Kyei-Baffour, N. Allometric models and aboveground biomass stocks of aWest African Sudan Savannah watershed in Benin. Carbon Balance Manag. 2016, 11, 16.
Bayen, P.; Noulèkoun, F.; Bognounou, F.; Lykke, A.M.; Djomo, A.; Lamers, J.P.; Thiombiano, A. Models for estimating aboveground biomass of four dryland woody species in Burkina Faso, West Africa. J. Arid. Environ. 2020, 180, 104205.
Moussa, M.; Mahamane, L.; Saadou, M. Allometric equations for biomass estimation of woody species and organic soil carbon stocks of agroforestry systems inWest African: State of current knowledge. Int. J. Res. 2015, 2, 17-33.
Kuyah, S.; Muthuri, C.; Jamnadass, R.; Mwangi, P.; Neufeldt, H.; Dietz, J. Crown area allometries for estimation of aboveground tree biomass in agricultural landscapes of western Kenya. Agrofor. Syst. 2012, 86, 267-277.
Leite, R.V.; Silva, C.A.; Mohan, M.; Cardil, A.; Almeida, D.R.A.D.; Jaafar, W.S.W.M.; Guerra-Hernandez, J.; Weiskittel, A.; Hudak, A.T.; Broadbent, E.N. Individual Tree Attribute Estimation and Uniformity Assessment io Fast-Growing Eucalyptus spp. Forest Plantations Usiog Lidar and Lioear Mixed-Effects Models. Remote Sens. 2020, 12, 3599.
Woomer, P.L.; Touré, A.; Sall, M. Carbon stocks in Senegal's Sahel transition zone. J. Arid. Environ. 2004, 59, 499- 510.

* cited by examiner

| Site | Variable | Formulation |
|---|---|---|
| ARCOS | Y=DBH. X=Crown | $y = 1.1621x^2 + 0.4647x + 13.61$ $R^2 = 0.4344$ |
| ICRAF | Y=DBH. X=Crown | $y = -0.0024x^2 + 2.437x + 5.3041$ $R^2 = 0.5167$ |
| RECOR | Y=DBH. X=Crown | $y = 0.2639x^2 + 0.5172x + 13.434$ $R^2 = 0.6526$ |
| Birdlife | Y=DBH. X=Crown | $y = -0.514x^2 + 6.3883x + 8.306$ $R^2 = 0.239$ |
| WAG | Y=DBH. X=Crown | $y = -0.0439x^2 + 5.2505x - 4.983$ $R^2 = 0.6684$ |
| WFZ | Y=DBH. X=Crown | $y = -0.0763x^2 + 4.4469x - 1.872$ $R^2 = 0.5824$ |
| ITF | Y=DBH. X=Crown | $y = 3.1163x - 0.0951$ $R^2 = 0.5541$ |
| DREK | Y=DBH. X=Crown | $y = 0.0581x^2 - 0.3989x + 19.029$ $R^2 = 0.214$ |
| MKEC | Y=DBH. X=Crown | $y = 2.2881x + 3.8482$ $R^2 = 0.4782$ |
| EPZ-Turk | Y=DBH. X=Crown | $y = -0.0285x^2 + 2.3305x + 1.6724$ $R^2 = 0.5868$ |
| FairTree | Y=DBH. X=Crown | $y = -0.0379x^2 + 1.4995x + 15.96$ $R^2 = 0.7594$ |
| Sadhana | Y=DBH. X=Crown | $y = 0.23561x + 3.3747$ $R^2 = 0.7942$ |
| KFT | Y=DBH. X=Crown | $y = 2.2377x + 3.4062$ $R^2 = 0.6761$ |
| KEV | Y=DBH. X=Crown | $y = 0.1713x^2 + 2.4385x - 1.0637$ $R^2 = 0.8466$ |
| ILEG | Y=DBH. X=Crown | $y = 0.0019x^2 + 2.7303x + 1.6132$ $R^2 = 0.7269$ |
| EPZ | Y=DBH. X=Crown | $y = 0.0066x^2 + 2.2531x + 5.6758$ $R^2 = 0.7304$ |
| GOSH | Y=DBH. X=Crown | $y = 0.2233x^2 - 0.95x + 8.526$ $R^2 = 0.6342$ |
| HERP | Y=DBH. X=Crown | $y = 0.0794x^2 + 1.1117x + 15.845$ $R^2 = 0.5976$ |
| CERATH | Y=DBH. X=Crown | $y = 0.1617x^2 - 0.5582x + 28.272$ $R^2 = 0.6473$ |
| PADO | Y=DBH. X=Crown | $y = 2.559x + 8.52$ $R^2 = 0.5007$ |
| SAFI | Y=DBH. X=Crown | $y = 0.0911x^2 + 2.1641x + 12.632$ $R^2 = 0.726$ |
| Kenya | MSU + Panzou | $y = 2.3667x + 4.5346$ $R^2 = 0.51$ |
| Ghana | MSU + Panzou | $y = 3.8312x + 2.9469$ $R^2 = 0.6207$ |
| Malawi | MSU + Panzou | $y = 4.131x – 23.5968$ $R^2 = 0.7888$ |

FIG. 11A

| Equation | Limits for DBH (cm) |
|---|---|
| AGB = 0.1612 * ((DBH^2)^1.193) | 5.0 to 48.2 |
| AGB = 1.703 + (1.915 * DBH) | 1.2 to 13.2 |
| AGB = -0.360 + (1.901*DBH) | 1.2 to 13.0 |
| AGB = 0.2411 * (DBH ^ 2) ^ 0.959 | 5.0 to 24.9 |
| AGB = 0.30 * (DBH)^2.31 | 2.6 to 180 |
| AGB = 0.10649 * (DBH)^2.5759 | 6 to 180 |
| AGB = 0.16502 * (DBH)^2.3351 | 3 to170 |
| AGB = 0.5158 * (DBH)^2.181 | 7 to 98 |
| AGB = 0.29543 * (DBH)^2.3085 | 2 to180 |
| AGB = 0.091 * (DBH)^2.472 | 3 to 102 |
| AGB = 0.085 * (DBH)^2.471 | <10 to >50 |
| AGB = 0.091 * (DBH)^2.472 | 2.5 to 102 |
| AGB = (0.248 * DBH^2) + (6.243 * DBH) - 15.45 | >0 to ≥10 |
| AGB = 0.5099 * (DBH^1.9141) | 11 to 155 |
| AGB = 0.064 * (µDBH^2.340) M. indica | <10 to >40 |
| AGB = 0.0638 * (DBH^2.5435) P. americana | <10 to >40 |
| AGB = 0.1428 * (DBH^2.2471) | <5 to >40 |
| AGB = 0.143 * (DBH^2.271) or 0.102 * (DBH^2.3) | 5 to 105 |
| AGB = 0.284 * (DBH^2.085) | 3 to 9 |
| AGB = 0.009 * (DBH^3.638 | 6 to 15 |
| ln (AGB) = -1.23 +2.16 * ln(DBH) | 10-15 |
| ln (AGB) = -2.68 +2.5 * ln (DBH) | 40-50 |
| AGB = 0.21691 * (DBH^2.318391) | 5.3 to 111.2 |
| AGB = (1.929 * DBH) + (0.116 * DBH^2)+(0.013 * DBH^3) | 5.15 to 41.5 |
| AGB = (5.066 * DBH) - (0.696 * DBH^2) + (0.053 * DBH^3) | 5-32 |
| AGB = (-3.524 * DBH) + (0.0.946 * DBH^2) - (0.01 * DBH^3) | 5-27 |
| AGB = (9.255 * DBH) - (1.563 * DBH^2) + (0.089 * DBH^3) | 5-42 |
| AGB = -2.97 * ((DBH^2*H)^0.930) | |
| AGB = exp(-2.6554) * DBH^2.26 | 11 to 57 |

FIG. 11B

| Carbon Pool | Description | Inclusion in Carbon Estimate |
|---|---|---|
| Above Ground Biomass (AGB) | Woody and Herbaceous Biomass of Living Vegetation Above the Soil Surface that Includes Trees, Shrubs, Palms, Bamboo, Vines, and Other Living Plants. | Directly Measured at Each Inventory Site |
| Below Ground Biomass (BGB) | The Biomass of Live Roots >2 mm Diameter that Includes the Coarse Roots Trees, Shrubs and Other Living Plants. | Default Value Used in Estimate |
| Dead Wood | Non-living Woody Biomass that is Larger than the Litter Pool. Deadwood Includes Both Standing Dead Wood and Down Dead Wood Lying on the Surface ≥15 cm Diameter. | Directly Measured at Each Inventory Site |
| Litter | Non-living Biomass on the Soil Surface that is Larger than Soil Organic Matter (>2 mm) and Smaller than the Dead Wood (<15 cm). | Not Measured and Excluded from Estimate |
| Soil Organic Carbon (SOC) | The Organic Carbon in Mineral or Organic Soils to a Specified Depth (30 cm is the Default Depth But Sometimes Measured Up to 1 m Deep) | Not Measured and Excluded from Estimate |

FIG. 14

FOREST MAPPING AND CARBON ESTIMATION SYSTEM AND METHOD FOR OPERATING THE SAME

GOVERNMENT FUNDING

This invention was made with government support 80NSSC20K0263 awarded by NASA; 80NSSC21K0315 awarded by NASA; AID-OAA-1-13-00058 awarded by USAID; and AID-386-C-12-00002 by USAID. The government has certain rights in the invention.

FIELD

The present disclosure relates to forest mapping and, more specifically, to a system and method for mapping forests and estimating the carbon absorbed by the same.

BACKGROUND

Forestry-related climate change mitigation measures can reduce future emissions and create removals of carbon from the atmosphere. As such, tropical forests now receive considerable attention in climate policy as a focal point for public and private investments, mostly in countries and regions with high biomass closed canopy forest. Examples include the Green Gigaton Challenge, Lowering Emissions by Accelerating Forest finance coalition (LEAF) and the Architecture for REDD+ Transactions (ART). An important emphasis has been placed on reducing deforestation and forest degradation rates to avoid emissions in the future, along with the regeneration of natural forests. However, the problem with focusing policies too narrowly on avoided future emissions is that there are few feasible decarbonization pathways to 2050 that do not have residual emissions which will require offsetting activities today. The most realistic decarbonization pathways do not reduce emissions rapidly or intensively enough to avert a 1.5° C. global average temperature increase, as stipulated by the Intergovernmental Panel on Climate Change and the Paris Agreements. Thus, many analyses conclude that a net-zero emission strategy is needed, where residual emissions can be offset by activities that remove carbon from the atmosphere in tandem with activities aimed at reducing emissions.

The concept of global net zero emissions is a way to describe balancing residual emissions of carbon dioxide with removals of carbon dioxide. Perhaps the best way to create carbon removals is through land-based activities that include enhancement of carbon sequestration in regrowing natural forests and in expanding the area and density of trees outside of forests (TOF) through forest and landscape restoration (FLR). Many non-forest landscapes have considerable tree cover, and much of these TOF lands are increasing biomass, representing potentially important sinks for carbon. South Asia is a particularly important region in this regard. Trees outside the forests (TOF) are defined by default, as all trees excluded from the definition of forest and other wooded lands. Trees outside the forest are located on "other lands" mostly on farmlands and built-up areas, both in rural and urban areas. A large number of TOF consist of planted or domesticated trees. TOF include trees in agroforestry systems, orchards and small woodlots. TOFs may grow in meadows, pastoral areas and on farms, or along rivers, canals and roadsides, or in towns, gardens and parks. Some of the land use systems include alley cropping and shifting cultivation, permanent tree cover crops (e.g. coffee, cocoa), windbreaks, hedgerows, home gardens and fruit-tree plantations.

Sequestration-focused climate change mitigation can be achieved with TOF systems, while also delivering livelihood and income benefits. The carbon sequestration potential of TOF has been reported by the IPCC and other studies, although monitoring and measurement of TOF carbon is challenging. At least one author has argued against the need for very high-resolution data which can be expensive and difficult to use for change detection, suggesting instead the use of lower resolution observations from platforms such as Sentinel-2 which is readily accessible, low cost and temporally dense.

SUMMARY

This section provides a general summary of the disclosure and is not a comprehensive disclosure of its full scope or all of its features.

In the present example, a system and method are provided that uses tree crown polygons that are automatically mapped using AI/ML tools and very high-resolution (VHR) satellite data (35 cm object mapping) for predicting the size of individual trees and their carbon content over continental landscapes. Deep time series analysis using our massive archive of satellite data allows for continuous monitoring of carbon changes, and thus precise estimation of carbon emissions and removals anywhere in the world.

The system and method allows organizing data for reporting entity-scale climate change mitigation efforts for net-zero targets, deforestation and regeneration mapping in tree systems and forests, inventory of trees in project areas, assessment of tree timber and non-timber product yields, and other applications. The system and method support information products for compliance with climate and sustainability government requirements (e.g. EU Deforestation Regulation, the US SEC climate risk disclosure). It also provides an entity with capabilities to deploy nature-based solutions (NbS) in supply chains, enabling much improved Scope 3 reporting. This technology platform is backed up with a host of carbon project sourcing tools for project developers and the carbon financial markets where tree planting, agroforestry and other NbS actions are important for carbon removals.

The system may be referred to as the Natsure.ai platform, which is cloud based system delivered over a database backed web frontend application. The backend contains modules for ground sampling frame allocation, field and tree data management, content management, allometric scaling including an equation library, carbon stock estimation, carbon stock change estimation, emissions and removal scenarios, remote sensing data acquisition at any scale and resolution, novel ML/AI processing of individual trees, mapping species, and high resolution mapping of deforestation and forest degradation. The Natsure.ai provides unique computational models for fraction cover and deep learning tree crown and carbon mapping and estimation. The models are trained classifier that may use artificial intelligence components.

In general, there are three process flow modules to Natsure.ai: 1) field data management with biomass calculators; 2) whole stand deforestation and forest degradation assessment and mapping with satellite remote sensing, and 3) individual tree crown detection, mapping and carbon stock estimation.

In one aspect of the disclosure, a method for generating a carbon map includes receiving at a satellite, reflected light from an object, forming high resolution satellite image data at the satellite, communicating the high resolution satellite image data to a pre-processing system, pre-processing the high resolution satellite image data to form pre-processed data, communicating the pre-processed data to a trained classifier, determining at the trained classifier a crown projected area for individual trees, determining a carbon stock for each of the individual trees at a processing system and determining a carbon map for the individual trees.

In another aspect of the disclosure, a method of determining a carbon map for an area includes receiving image data, generating crown polygons for crowns of trees outside of forests at a machine learning model, determining a crown area from the crown polygons, determining a diameter at breast height based on the crown polygon using an allometric model and generating a carbon map based on the diameter at breast height using a diameter at breast heigh allometry model.

In another aspect of the disclosure, a method of determining a carbon map for an area includes receiving moderate resolution image data of a landscape area comprising a plurality of pixels, determining tree pixels for trees at a machine learning model, determining fractional pixels and generating a carbon map based on the tree pixels and fractional pixels.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 11A is a table for determining the diameter at breast height for trees based upon the crown area.

FIG. 11B is a table for the relationship of the above ground biomass versus the diameter at breast height.

FIG. 14 is a table with carbon pool data.

Corresponding reference numerals indicate corresponding parts throughout the several views of the drawings.

DETAILED DESCRIPTION

Figure 1:
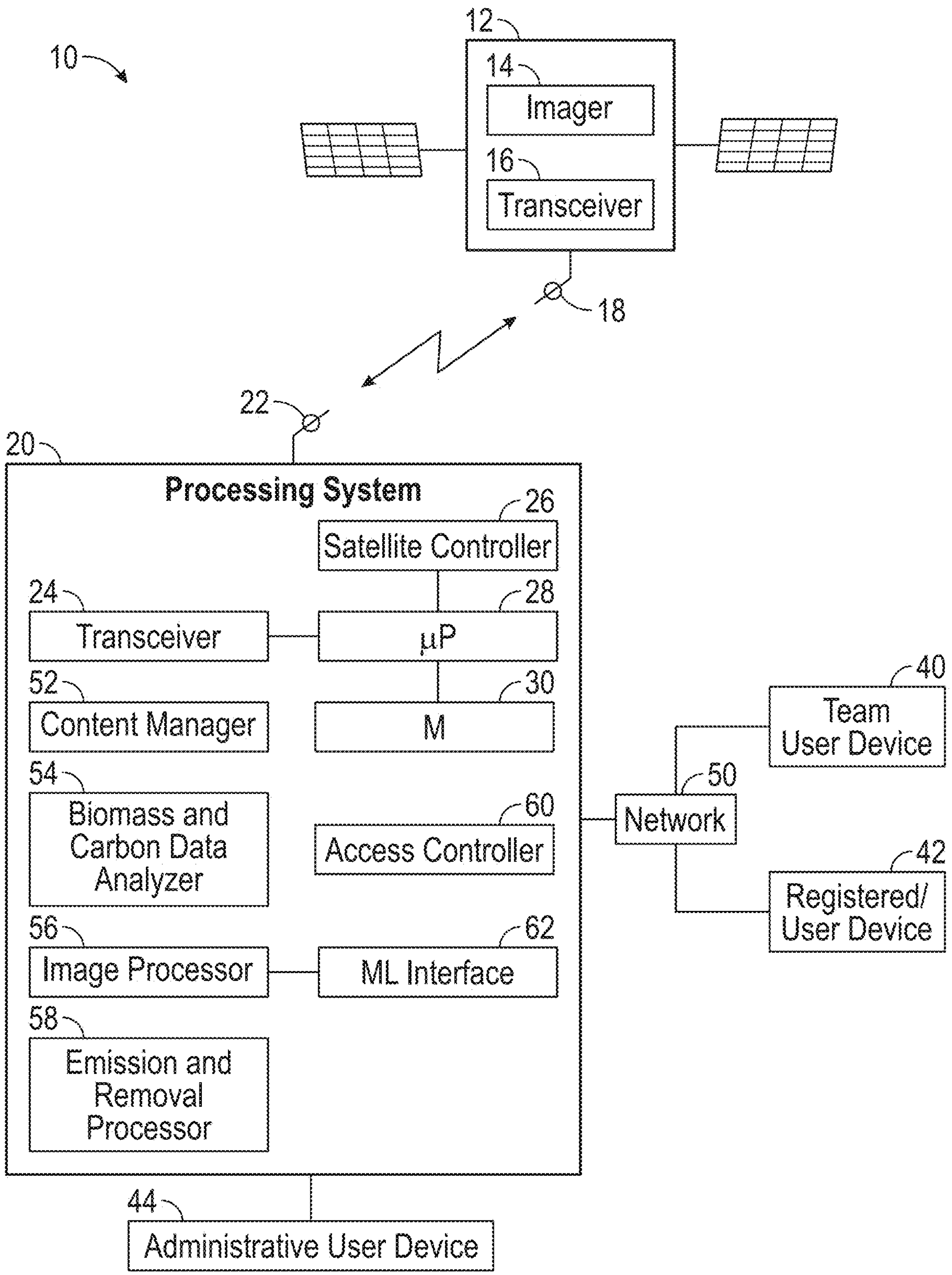
FIG. 1 is a high level block diagrammatic view of the system according to the present disclosure.

Example embodiments will now be described more fully with reference to the accompanying drawings.

Various definitions are used in the following description.

Landscape—Large scale multipurpose areas of land that may include several land-use categories such as forests, grasslands, savannas, agriculture, croplands, and settlements. Generally measured in km2 and normally an area greater than 40,000 ha. An area of interest is a smaller portion of the landscape.

Trees outside of forests (TOF)—Often referred to as trees on farms, a more specific definition Includes landscapes of trees not formally included in the forest zone, which is often defined officially as recorded forest area, gazetted forest, forestlands, or other designations, and which may include occurrences of (1) sparse woodlands and savannas with canopy cover less than the forest definition; (2) agricultural landscapes with individual remnant or planted trees on farms; (3) agroforestry systems that combine perennial trees with annual crops, 4) small holder plantations, 5) orchards, 6) woodlots and other widely spaced or individually grown tree-based systems.

Forest—Land with tree crown cover (or equivalent stocking level) of more than 10% and area of more than 0.5 ha. Trees should be able to reach a minimum height of 5 m at maturity in situ.

Project—The entire geographic area where a project developer is paid to restore land. A project can consist of a single site or of multiple sites or may be a landscape in which the project developer is providing materials or assistance. It may be a specific area or areas of intervention with specific boundaries for planting, regeneration, enhancement or conservation or an area or areas without specific identification of intervention such as an individual farm property, regeneration target zones, riparian corridors, and so forth.

Restoration Area—Refers to each separate, contiguous area on the ground where restoration work is being done, either specifically delineated or generally targeted. In some cases, restoration is being done contiguously and uniformly within specifical boundaries or more broadly and irregularly within and across a land unit. Each restoration area will be represented by a point of a polygon for use in TerraMatch's monitoring system depending on the context.

Site—The basic unit for organizing and reporting biophysical data on Terramatch. It is a single restoration area, or a grouping of restoration areas based on proximity and/or common characteristics. A site may contain multiple target land use systems, restoration practices, and target tree distributions but is always specific to a single planting year.

Target Land Use System—The land use system(s) that will exist after 6 years of project implementation, not the current state of the land or the state of the land as it transitions to its final use. These comprise of Agroforest, Mangrove, Natural Forest, Open Natural Ecosystem, Silvopasture, Riparian Area/Weland, Urban Forest, and Woodlot/Plantation.

Target Tree Distribution—How trees will be spread throughout the site after restoration work has concluded.

Referring now to FIG. 1, a block diagram of the nature.ai system 10 (or simply, system 10) for determining carbon dioxide removal factor is set forth. A satellite 12 is used to generate high resolution satellite image data. In particular, an imager 14 such as a charge coupled device (CCD) is used to generate the high resolution satellite image data. The image data may comprise more than one spectral band such as at least three spectral bands. The spectral bands, in this example, include but are not limited to red, green and blue (RGB). In the present example, 0.35 meter spatial resolution was used. The image data in the three (or more) spectral bands are communicated though a transceiver 16 (transmitter/receiver or transponder) and an antenna 18.

A processing system 20 having an antenna 22 receives the high resolution satellite image data which is received at a transceiver 24. The transceivers 16, 24 may intercommunicate therebetween. Telemetry signals, command signals and control signals may be exchanged using a satellite controller 26 in the processing system 20. For example, signals may be communicated with the satellite 12 to point in a certain direction and obtain image data from reflected light at the imager 14.

A microprocessor or processor 28 is illustrated coupled to the memory 30. Although one processor 28 is illustrated several may be used in the system 10. The memory 30 may be a non-transitory computer-readable medium that includes instruction that are executable by the processor 28. The instructions may include instructions for controlling the satellite controller 26, controlling the content, image processing, determining of biomass and carbon and the removal thereof, and communicating with a team user device 40, a registered user device 42 and an administrator user device 44 through a network 50. The memory 30 may store various types of data used at the processing system 20 including but not limited to high resolution satellite image data received from the satellite 12.

The system 10 provides four core capabilities for processing and managing spatial and inventory data within two broad user and application categories such as supporting project scoping, development and planning and supporting project, measurement, monitoring and reporting.

The core processing capabilities of the processing system 20 include content management at a content manager 52 which includes shared and distributed content and field data. Another capability of the processing system 20 includes managing and analyzing field level biomass and tree measurement data in the biomass and carbon data analyzer 54. Yet another capability of the processing system 20 is image processing, geographic information system (GIS) spatial mapping, and geospatial data management in an image processor 56. Another capability of the processing system 20 is carbon emissions and removal estimation and monitoring reporting in an emission and removal processor 58.

The content manager 52 allows project managers and team participants to upload documents, data, data products, and data analysis into the processing system 20 for team-wide access to project information. Registered user devices 42 log in to the processing system 20 to access and work with project information. The system 20 can set and restrict access privileges using an access controller 60. Functions generate reports in PDF format for distribution and workflow and task management.

The biomass and carbon data analyzer 54 organizes, manages and analyzes field level biomass and carbon data. It allows users to upload plot level tree measurement data into a relational database to then calculate biomass carbon density and carbon stocks for each stratum within a project. Natsure.ai manages a library of allometric scaling equations, to calculate above ground and below ground biomass carbon at the forest stand level or for individual trees. Users must basic forest inventory measurements such as tree species, diameter and breast height, and sample plot area.

Image processor 56 is used for processing remote sensing image data, GIS mapping, and geospatial data management. This includes a machine learning interface 62 for detecting individual tree crowns by processing sub 1-meter satellite data. It processes satellite data to produce individual tree-crown maps, and combines it with allometric scaling models based on the equations contained in a library. The technology application also processes satellite data for mapping stands of trees in forests at resolution of 3-10 m. The mapping capabilities allow users to draw and store project area boundaries, parcel or strata areas, and field data plot locations, and produce tree/stem counts. Also processing capabilities allow for integrating field-based tree measurements from sample plots with biomass data maps and project strata maps. In the present example, different resolutions for the image data were studied. 10 m resolution Sentinel-2 data and 0.35 m very high-resolution (VHR) Worldview and GeoEye data were used.

The image processor 56 obtained analysis-ready Sentinel 2 VINR Level 2 data. Clouds were detected and removed. A monthly composite dataset was obtained by averaging all cloud free data available for each month. The 12 month data was averaged across all months to produce a final composite dataset.

The emission and removal processor 58 is used for carbon and other greenhouse gas emissions and removals estimation, monitoring and reporting. One feature is processing functions to calculate emissions and removals from land cover changes in forestry, agriculture, and other land uses. The emission and removal processor 58 allows users to input field inventory data to describe the carbon stocks associated with their area of analysis. In project scoping and planning the process runs ex ante scenarios. In project measurement, monitoring and reporting the process function report ex post emissions and removals using multi-date measurement data from field inventories and remote sensing biomass data products. Delivery is through a spatially-enabled web GIS function.

The system 10 more than a simple web portal providing access to GIS data sets. It includes a system of processes for managing project data, making field and remote sensing measurements, and reporting of results in standard text and web-GIS formats, delivering decision-ready intelligence for decarbonization policy, risk assessment, disclosure and compliance. In addition to providing carbon intelligence, it can be used for almost any forest application, including natural areas management, planned conversion, restoration initiatives, urban tree management, and so forth. Any project that will have an impact on forest cover (either positive or negative) can use the tools to help minimize emissions or provide carbon dioxide removals. These processes allow project developers to determine best case options in a range project activities.

Overall, the Natsure.ai system 10 provides three methods that may be used together to provide an improved biomass determination. The first method is used for collecting, organizing and processing of field data related to allometric scaling and biomass estimation for forests and trees outside of forests is performed.

The second method performs processing of very high resolution satellite data to map biomass and carbon in individual trees based on individual tree crown mapping using deep machine learning and allometric scaling from canopy-based allometry. The second method processes high resolution satellite data (<1 m) using deep machine learning models to detect individual tree canopies. Tree biomass estimates are assigned to each tree, based on tree crown mapping and the biomass allometry. The precise crown polygon for individual trees outside of forests is mapped. Pre-processing of all very high-resolution data is done to correct for top of the atmosphere and surface reflectance, as well as geometry, radiometric sharpening, compositing and mosaicking.

The third method processes medium resolution satellite data (3-10 m) using deep machine learning to detect large clusters of trees and stands of forests, including medium resolution individual tree detection without mapping the crown object as is done in the second method. This module also maps tree cover density using the Fractional Cover algorithm (fC). This module estimates stand-level biomass from sample inventory statistics and adjusts the pixel-level estimate based on fC values. This module is where the pre-processing of all medium resolution data is done to correct for top of the atmosphere and surface reflectance, as well as geometry, radiometric sharpening, data compositing and mosaicking.

The third method is used for processing field collected allometric scaling data using a sample framework of fixed radius plots. The data collected from the plots are used to build an allometric model to calibrate a crown-based measure of individual tree biomass or to obtain a sample estimate to calibrate a stand-based measure of forest biomass. This Module manages tree and stand data, as well as all other content. It contains a calculator to estimate emissions and removals and provides a way for generating online maps of landscape carbon.

Figure 2A:
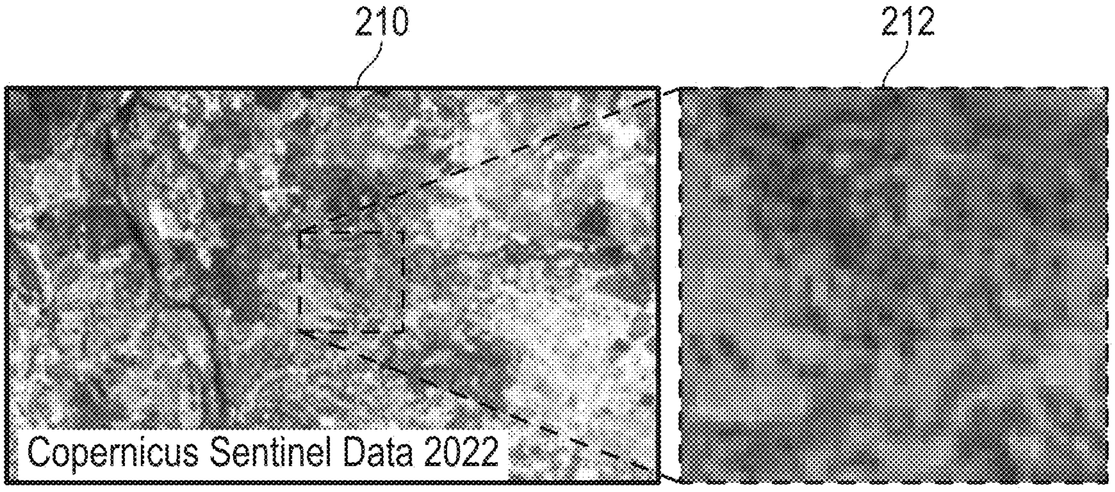
FIG. 2A is a moderate resolution plot of a landscape.
Figure 2B:
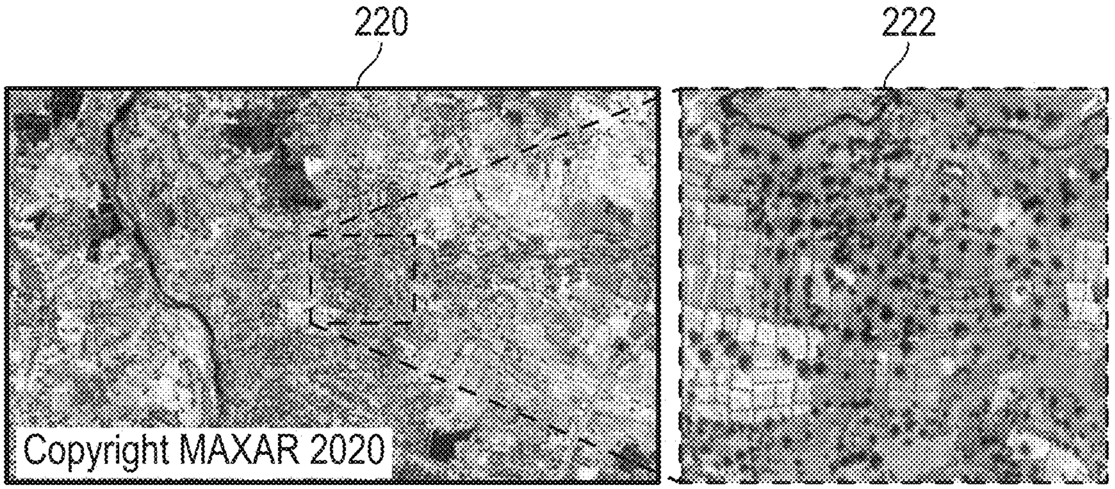
FIG. 2B is a very high resolution plot of the landscape of FIG. 2A.

Referring now to FIGS. 2A and 2B examples of moderate resolution (MR) image 210 with an enlarged portion *212a* and very high resolution image (VHR) 220 with an enlarged portion 222 is set forth. In this example, the Natsure.ai system 10 uses 10 m resolution Sentinel-2 data and 0.5 m very high-resolution (VHR) data from Worldview and GeoEye satellite platforms to detect and map individual tree. Sentinel 2 data is too coarse to map individual tree crowns, because the pixel size (100 m2) than most tree crowns, but it can readily detect isolated trees. Clouds need to be detected and removed. Sentinel-2 is a deep time series dataset with frequent coverage globally, so there is a vast number of individual scenes. With this deep time series and massive availability Natsure.ai system 10 produces a monthly composite for a single year by averaging all cloud free data available for each month. The 12-month data were averaged across all months to produce a final composite dataset for any year. Natsure.ai system uses a UNet deep machine learning convolutional neural network model to detect pixels with individual and clusters of trees.

The VHR satellite data can be acquired at 0.35-0.5 m resolution, which means it can be used to detect and precisely map individual tree objects and produce polygons of individual tree crowns; time series and compositing is more difficult that with Sentinel-2, so mapping is done for a single image. The system generates maps of individual tree crowns at 0.5 m resolution using a UNet deep machine learning model with a ResNet encoder. The VHR data are predominantly from MAXAR satellites, specifically WorldView-2, WorldView-3, and GeoEye-1.

The data have spatial resolution ranging from 1.5 meters to 2 meters in the multispectral bands. These data were sharpened to 0.5 meters using the panchromatic band. Using a nearest neighbor diffuse pan sharpening algorithm to produce a pan-sharpened, orthorectified, three-band dataset.

A training dataset for 10 m Sentinel-2 mapping of TOF tree cover, is assembled from samples OF VHR data, representing 10-24% percent of an analysis area using samples of 256 by 256 pixels, or 6.56 km2. The training datasets are developed for both VHR and Sentinel-2 machine learning models. VHR labels are obtained from samples of land areas with trees, but not forests. Each sample was 128 by 128 pixels. Training sets are created from by manually labeling trees. Of the training samples, 10% are set aside for model testing. The model is trained for 15 epochs, where both loss (RMSE) and accuracy compared to the testing set converged to 0.2 and 0.95 respectively.

Figure 3A:
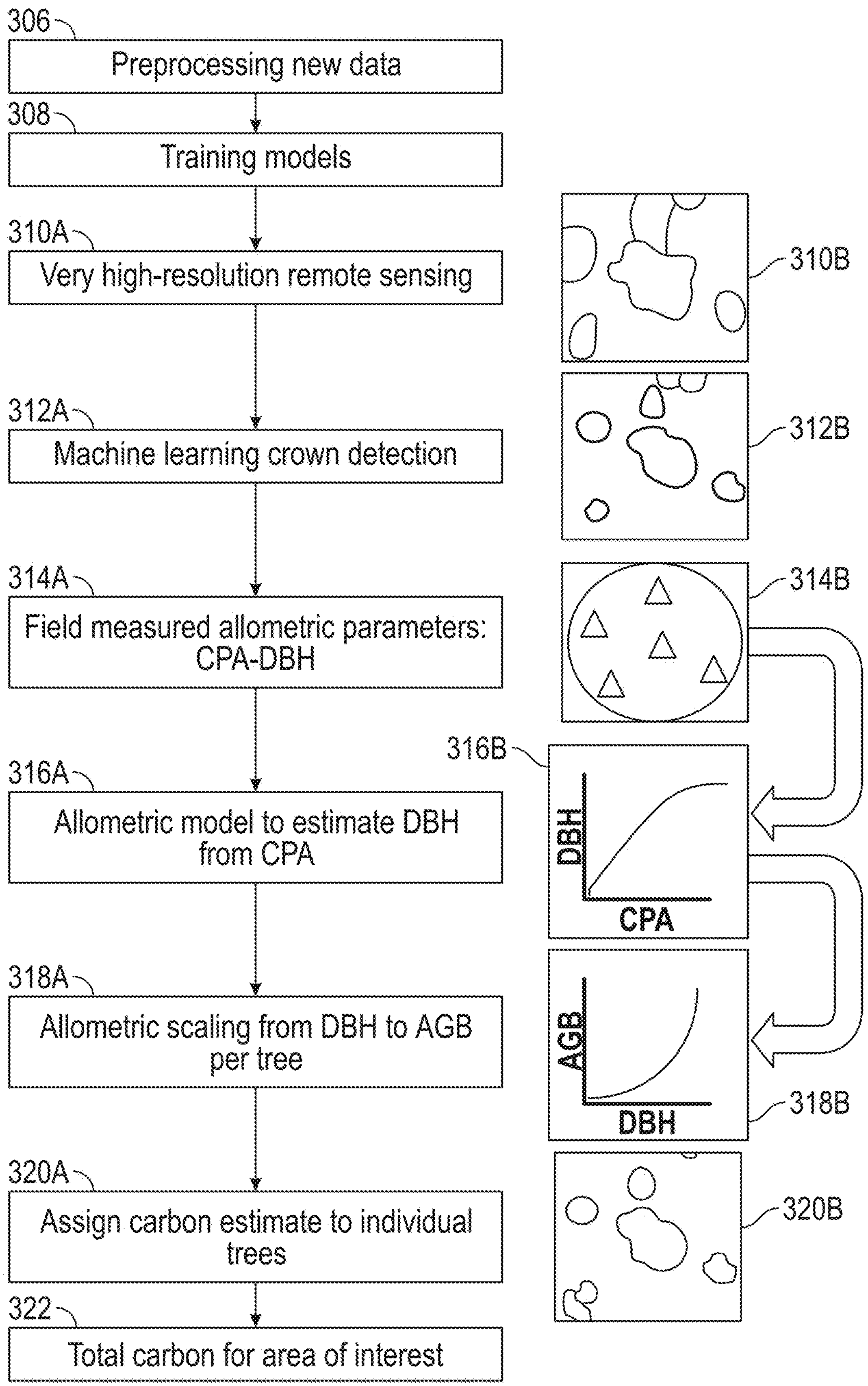
FIG. 3A is a high flowchart of a method for determining carbon for an area of interest.
Figure 3B:
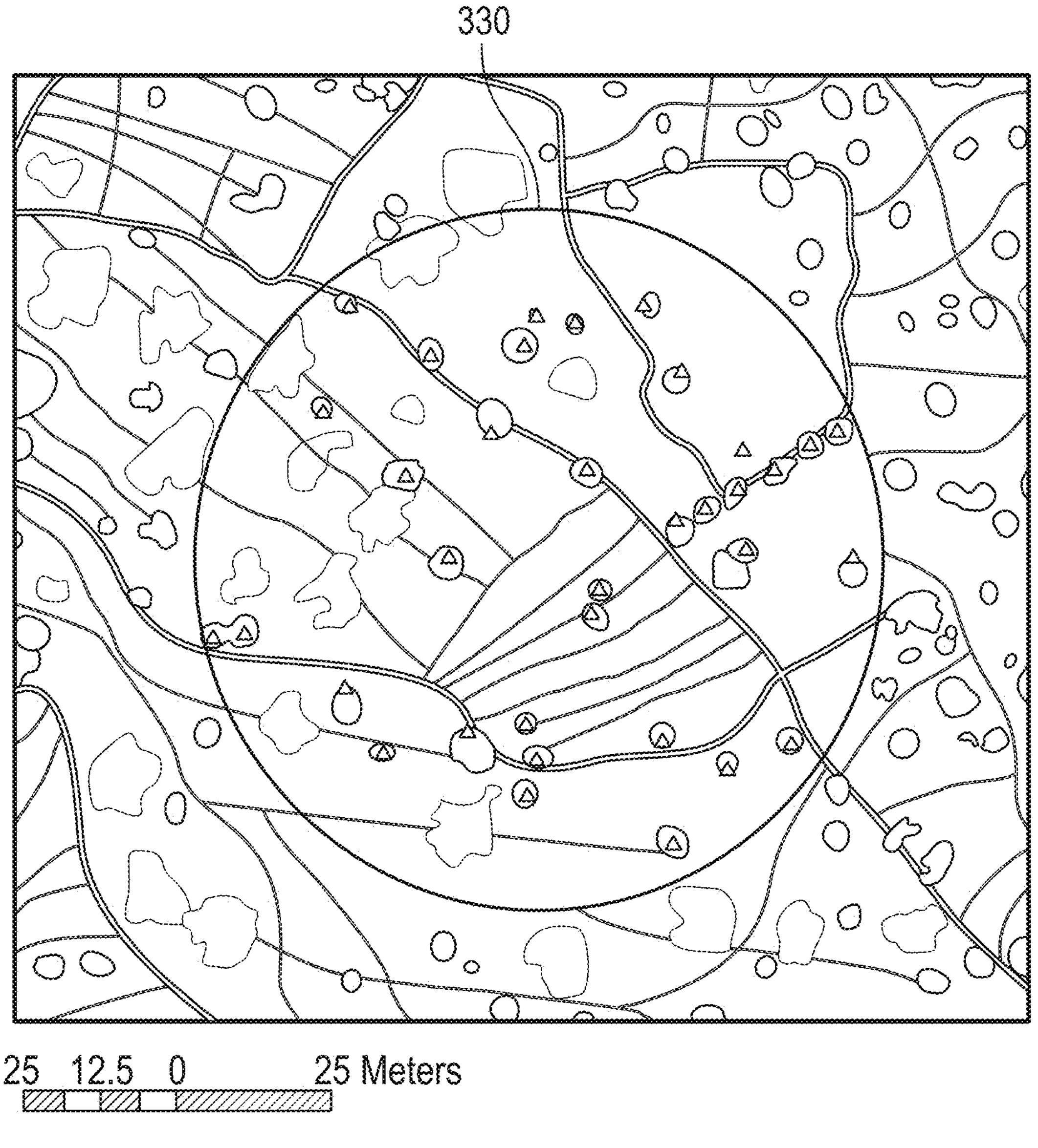
FIG. 3B is a landscape with an area of interest.

Referring to FIGS. 3A and 3B, a high-level flow chart along with corresponding images are illustrated. The processing of very high resolution (VHR) satellite data to produce maps of individual tree biomass and carbon maps at the landscape scale involves several steps, beginning with pre-processing of the raw satellite data in step 306, training deep machine learning models in step 308, running the machine learning models against the satellite data input layers in step 310A,310B for producing exact polygons of tree crowns in step 312A, 312B to allow extraction and separation of individual isolated trees from trees in forest stands.

The polygons are then assigned carbon values by developing allometric scaling models based on tree crowns. This stage of carbon attribution is done through a protocol that uses selected field-collected allometric parameters from sample plots in step 314A, 314B, which is used to develop an allometric scaling model from the translation of crown areas to stem diameter. The crown projected area (CPA) from the polygon is used to obtain the stem diameter breast height (DBH) in step 316A, 316B. This allometric relationship is then conjoined with an ordinary allometric model based on stem diameters taken from published literature. The stem diameter model can also be obtained using standard destructive sampling methods. Ultimately The DBH can be used to determine the above-ground biomass (AGB) in steps 318A, 318B. A carbon estimate can be determined in step 320A, 320B. Further details are provided below.

In FIG. 3B, an area of interest 330 may be evaluated during the process. Each tree in the area of interest 330 may be evaluated to obtain a total carbon for the area of interest in step 322.

Figure 4:
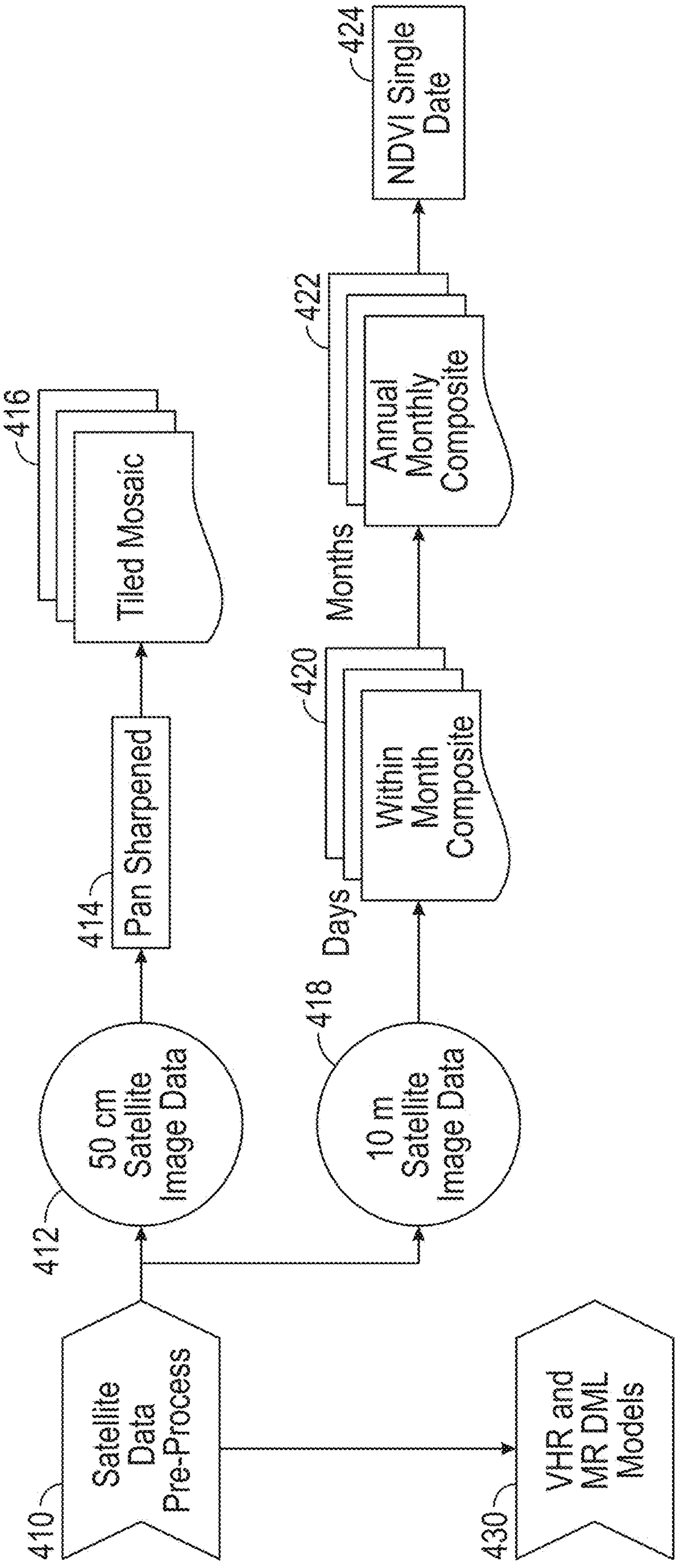
FIG. 4 is a high level method for obtaining a tile mosaic and NDVI for an area of interest.

Referring now to FIG. 4, a specific description of the processing flow for mapping individual tree carbon using VHR satellite data, deep machine learning (DML) and allometric scaling (AS) is set forth. The VHR data process and the MR data process may use the same deep machine learning but scaled to different resolutions, and different models for biomass and carbon attribution. For carbon attribution, the VHR method uses individual tree allometric scaling, and the MR uses a stand averaging method due to different scales and to alleviate the problem of tree crowns overlapping.

In the preprocessing process, in step 410, data is provided from the satellite. In step 412, the 50 cm (0.5 m) satellite data is obtained and pan sharpened in step 414. The pan sharpened data and the images associates therewith form a tile mosaic in step 416. For moderate process data, step 418 obtains 10 mm satellite data image and generates composites over a plurality of days which forms a month's composite in step 420. An annual composite uses the month data to form annual composites in step 422. Data for the area is used to obtain a normalized difference vegetation index (NDVI) at step 424. The satellite data may also be used to form VHR and MR digital machine learning models in step 430.

Figure 5:
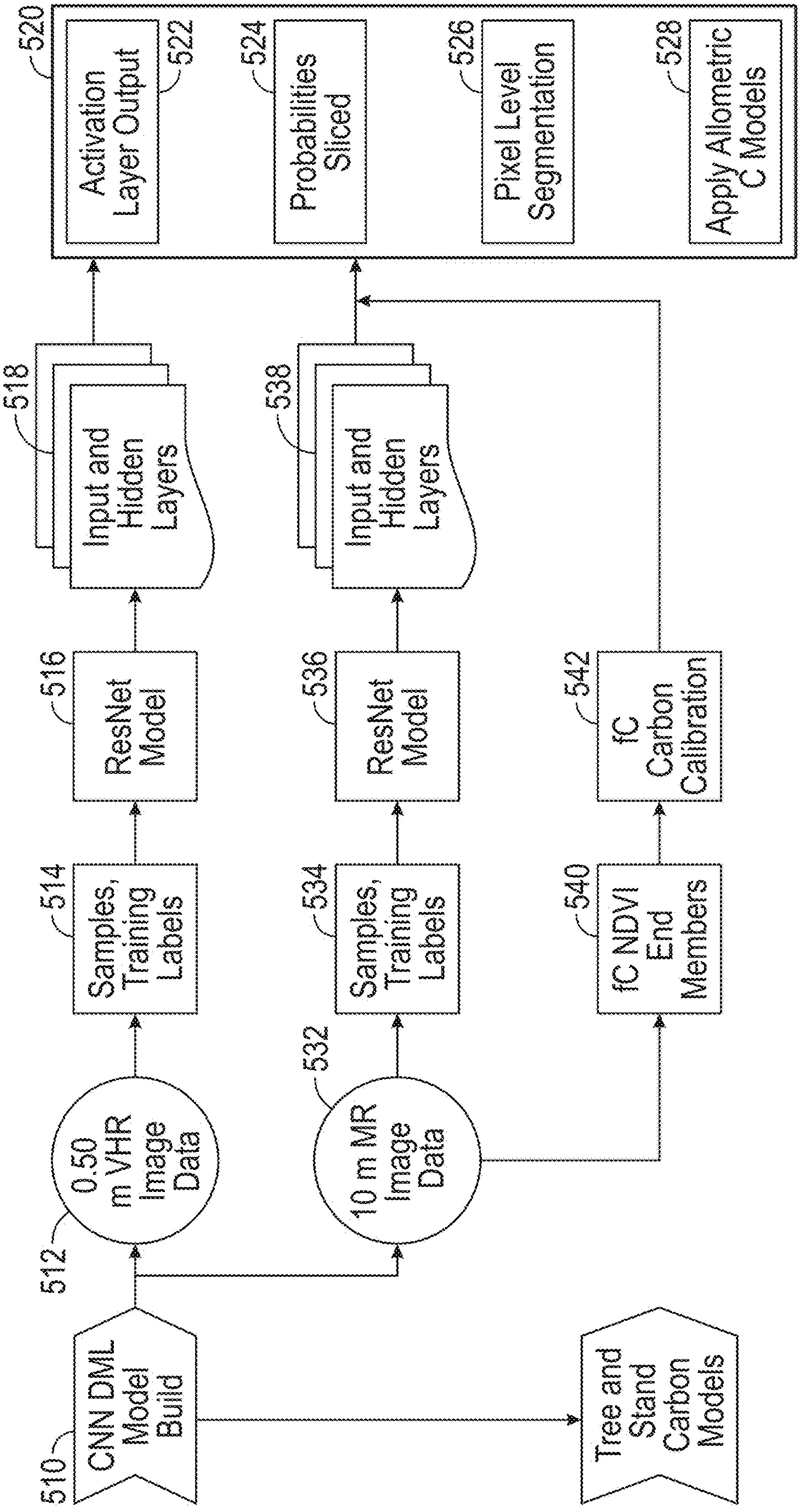
FIG. 5 is a high level method for moderate and high level resolution model building.

Referring now to FIG. 5, a convolution neural network digital machine learning model build process in illustrated in detail and begins at step 510. In step 512, the very high resolution image data is obtained. Samples and training labels are obtained in step 514. A ResNet model 516 is used to obtain input and hidden layers in step 518 to form the model 520 that has an activation layer out 522, probabilities sliced in step 524, pixel like segmentation in step 526 and allometric C models are applied in step 528.

The system also performs a similar generation of the model 520 but for moderate resolution images, which are obtained in step 532. Step 534 obtains samples and training labels. In step 536, the ResNet are used to obtain input and hidden layers in step 538. As well, step 540 is used to determine fractional coverage normalized difference vegetation index members. In step 542, the fractional coverage may be used to obtain a carbon calibration in step 542 which is used to form the model for the moderate resolution data.

A deep machine learning framework selection is now described. The task is to perform accurate image segmentation, which involves delineating objects or regions within images at the pixel level. UNet deep learning framework is used in this example.

Traditional machine learning algorithms such as Support Vector Machines (SVM), Random Forest (RF), and XGBoost (Extreme Gradient Boosting) have notable limitations when applied to image segmentation tasks. For example, feature engineering dependency is one example. Traditional machine learning algorithms such as SVM, Random Forest, and XGBoost depend significantly on manually crafted features, a process that is often intricate and time-consuming, particularly for tasks encompassing complex images characterized by diverse textures and shapes.

Another drawback of other algorithms includes limited Spatial Context: SVM, RF, and XGBoost typically make decisions based on isolated features or patches within the image, rather than considering the holistic spatial context. This can result in suboptimal performance when trying to segment objects with intricate boundaries or irregular shapes.

Scalability and memory requirements of other machine learning processes are another drawback. That is, RF and XGBoost build ensembles of decision trees, which can consume significant memory, particularly when dealing with high-dimensional feature spaces or large datasets. SVM's computational complexity can also pose challenges in scalability, especially when applied to large-scale image segmentation tasks.

Deep learning architectures like UNet and ResNet50 are compelling frameworks used in the present example to alleviate challenges posed by traditional machine learning methods including hierarchical feature learning. UNet and ResNet-50 are designed to automatically learn hierarchical representations of features directly from raw pixel data. This capability allows them to capture both low-level details (such as edges and textures) and high-level features (such as shapes and structures) crucial for accurate segmentation.

Another positive feature is spatial context integration. UNet's architecture, with its symmetric encoder-decoder structure and skip connections, facilitates the integration of fine details from the encoder path with contextual information from the decoder path. This enhances segmentation accuracy by preserving spatial context throughout the process. Depth and residual connections are also improved: ResNet-50, known for its depth and use of residual connections, can effectively capture complex features across multiple levels of abstraction. The skip connections in ResNet-50 mitigate the vanishing gradient problem, enabling training of very deep networks, which is beneficial for tasks requiring detailed and nuanced image segmentation.

Pixel-wise predictions are also permitted with both UNet and ResNet-50. They excel in producing dense predictions, where each pixel in the image is assigned a specific label or class. This capability is essential for tasks that demand precise segmentation at the pixel level.

Accurately segmenting images and preserving detailed information like shapes and textures, deep learning models like UNet and ResNet-50 perform better than traditional methods such as SVM, RF, and XGBoost. The models developed are best at learning intricate patterns directly from data, making them essential for advanced computer vision tasks and image analysis.

Figure 6A:
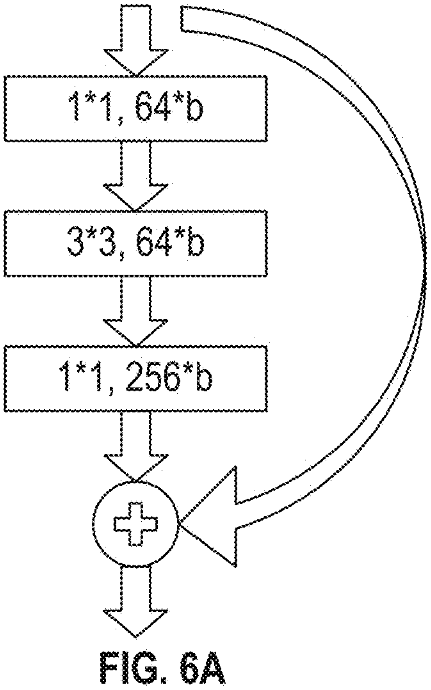
FIG. 6A is a block diagrammatic view of a UNet backbone.
Figure 6B:
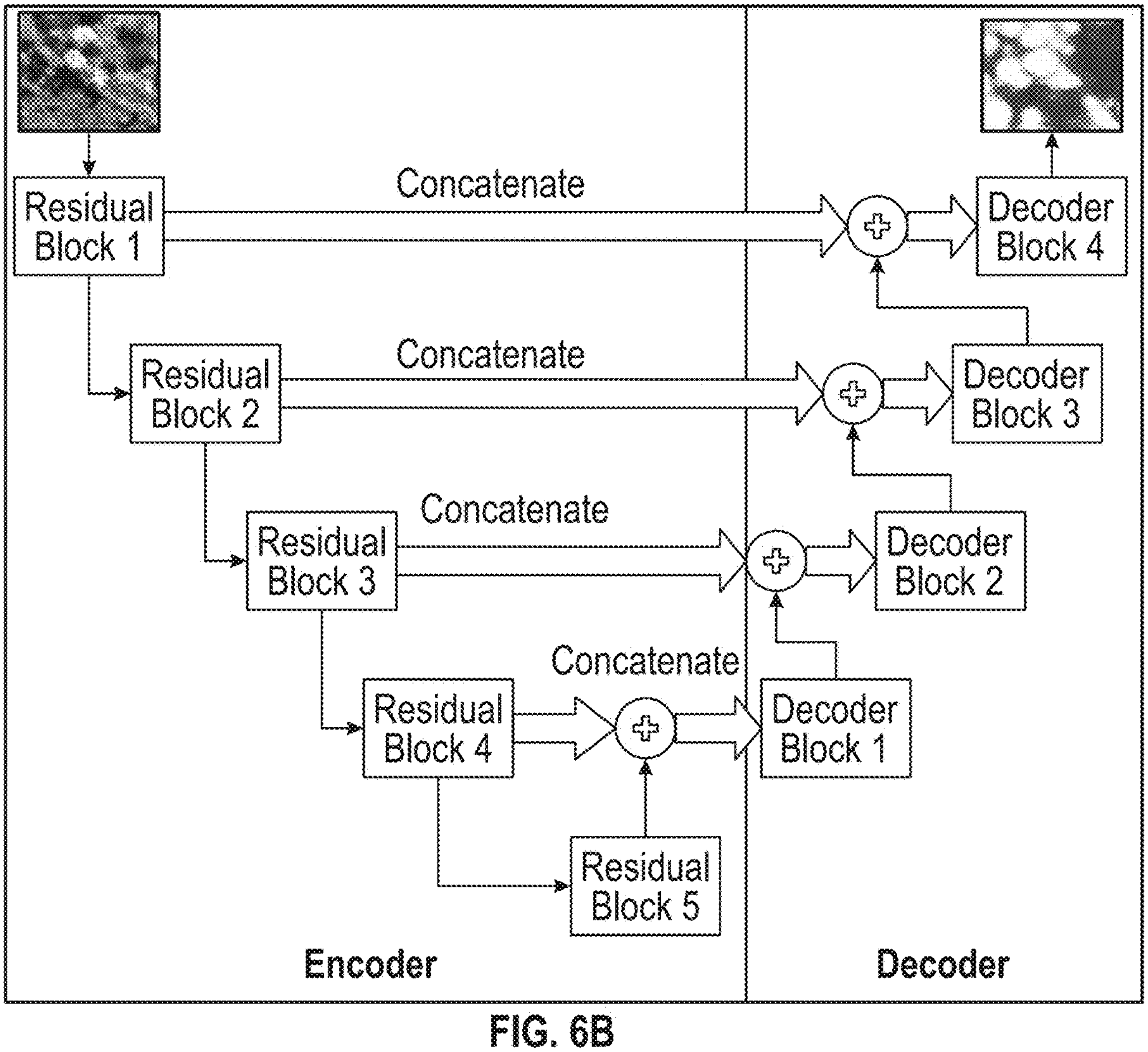
FIG. 6B is a block diagram of a UNet showing an encoder and decoder.

Referring now to FIGS. 6A and 6B, process flows for a UNet backbone are set forth. To get the best possible performance and compute speed with the compute-intensive VHR 0.5 m mapping a ResNet50 residual neural network model is inserted as the encoder in the UNet backbone. The choice of a ResNet encoder assumes that a UNet model would perform well detecting tree cover at 10 m resolution where data pixels are coarser resolution than individual trees, but less effective at a pixel resolution which is less than the resolution of individual tree-objects and individual tree crown polygons. Furthermore, the ResNet encoder performs better than UNet encoder in complex high-resolution images. In particular, it is better able to separate tree crowns from shrubs and tree clusters, decreasing commission and omission errors. The VHR individual tree crown polygons product is used as a reference dataset to evaluate the spatial accuracy of the MR map of TOF cover detection.

To analyze very detailed 0.5 meter resolution data a machine-learning model is trained on high-resolution images. These images are initially between 1.5 meters to 2 meters in resolution but were enhanced to 0.5 meters using the NNDiffuse algorithm. Training labels are purposely selected from various environments such as villages and farmlands, outlining polygons around individual tree crowns in hundreds of 200 meter by 200 meter sample areas across the landscape.

Within these areas, the training dataset is further divided the images into smaller 128 pixels by 128 pixels sections. These sections contained three-band images (RGB) as features and manually drawn polygons as labels. Any features or labels with missing data are removed to ensure effective learning across different landscapes.

For tree cover prediction and mapping, the U-Net deep learning architecture is employed as illustrated in FIGS. 6A and 6B, incorporating ResNet50 as its backbone. ResNet50 was chosen for its proven superior performance in image segmentation tasks, supported by its utilization of residual connections that effectively address challenges like vanishing gradients common during intensive training phases.

The model is initialized with pre-trained weights from ImageNet to leverage transfer learning and was optimized using the Adam optimizer with binary cross entropy as the loss function.

The model processes VHR images measuring 64 meters by 64 meters with a 0.5 meter resolution. Processing is done on suitable GPU computational blocks, such as an AMD 20 GPU provided by Michigan State University's High-Performance Computing Clusters. The trained model is applied to ortho-rectified, pan-sharpened, three-band VHR images split into 128 pixels by 128 pixels sections for tree prediction and mapping.

During evaluation, the pre-trained model sometimes generated unclear predictions along borders. To address this, we applied image flipping, predicting each tile three times on different axes and averaging the results to improve clarity. Post-prediction, we seamlessly merged and trimmed individual predictions to fit defined boundary areas.

Figure 7A:
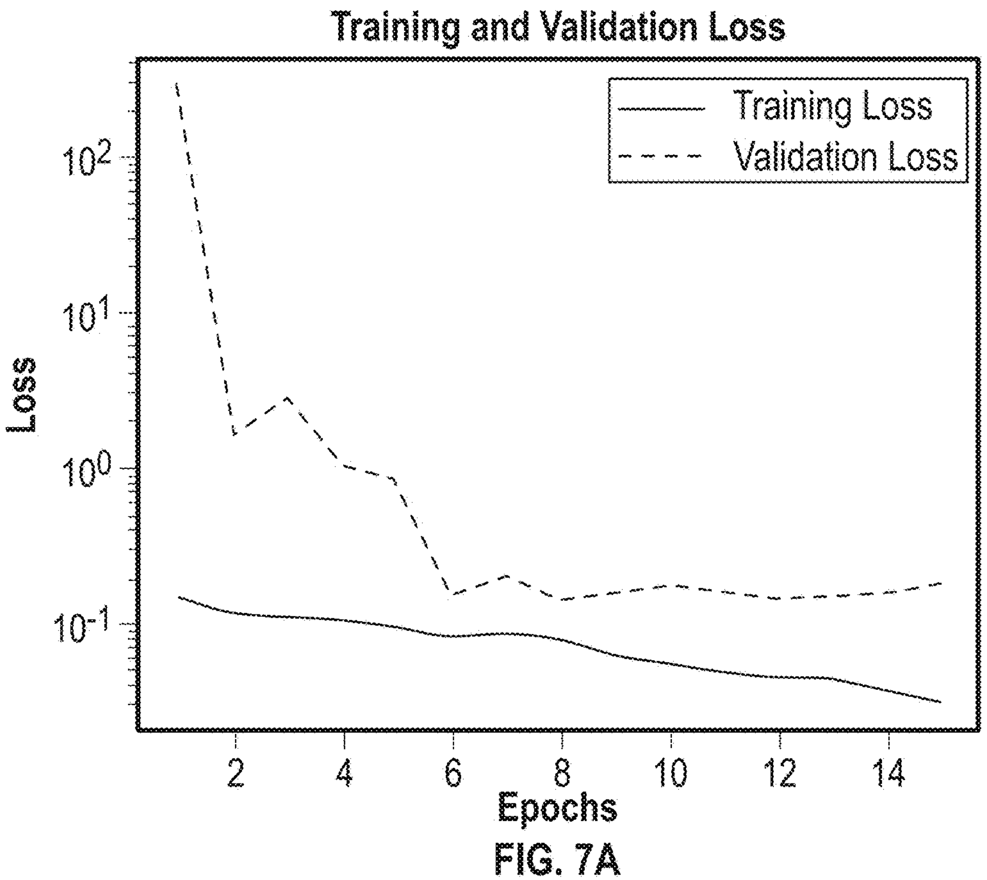
FIG. 7A is a plot for loss versus the number of efface for training and validation loss.
Figure 7B:
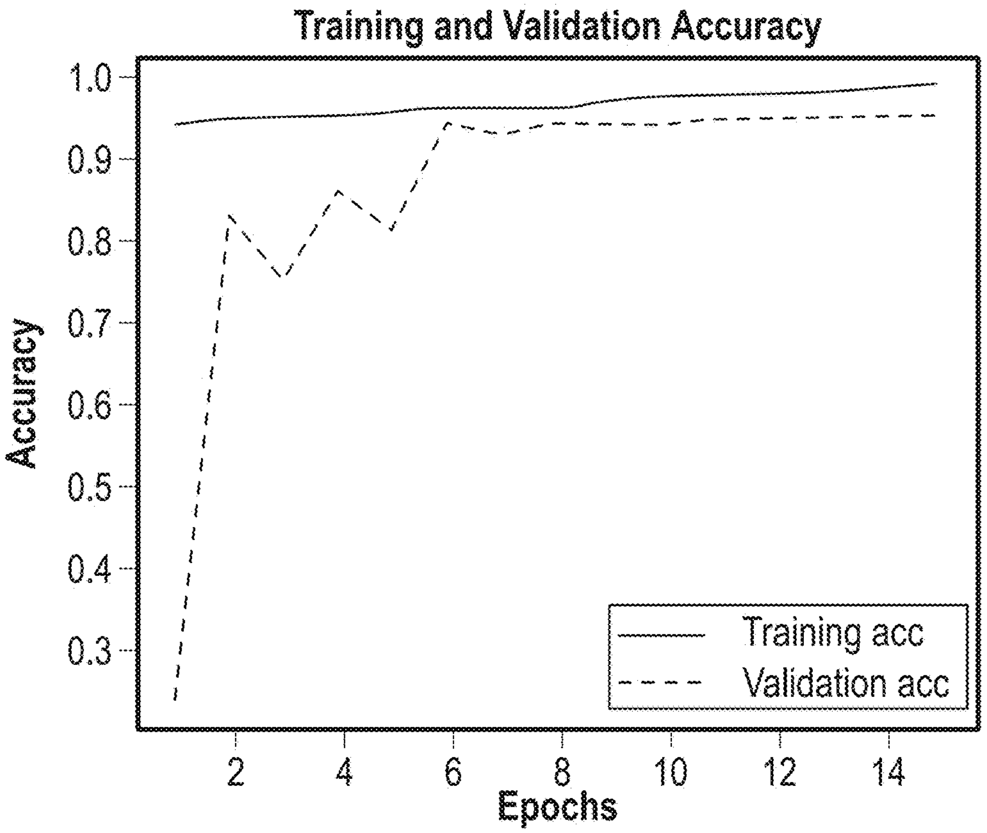
FIG. 7B is a plot of accuracy versus epics for training and validation accuracy.
Figure 8:
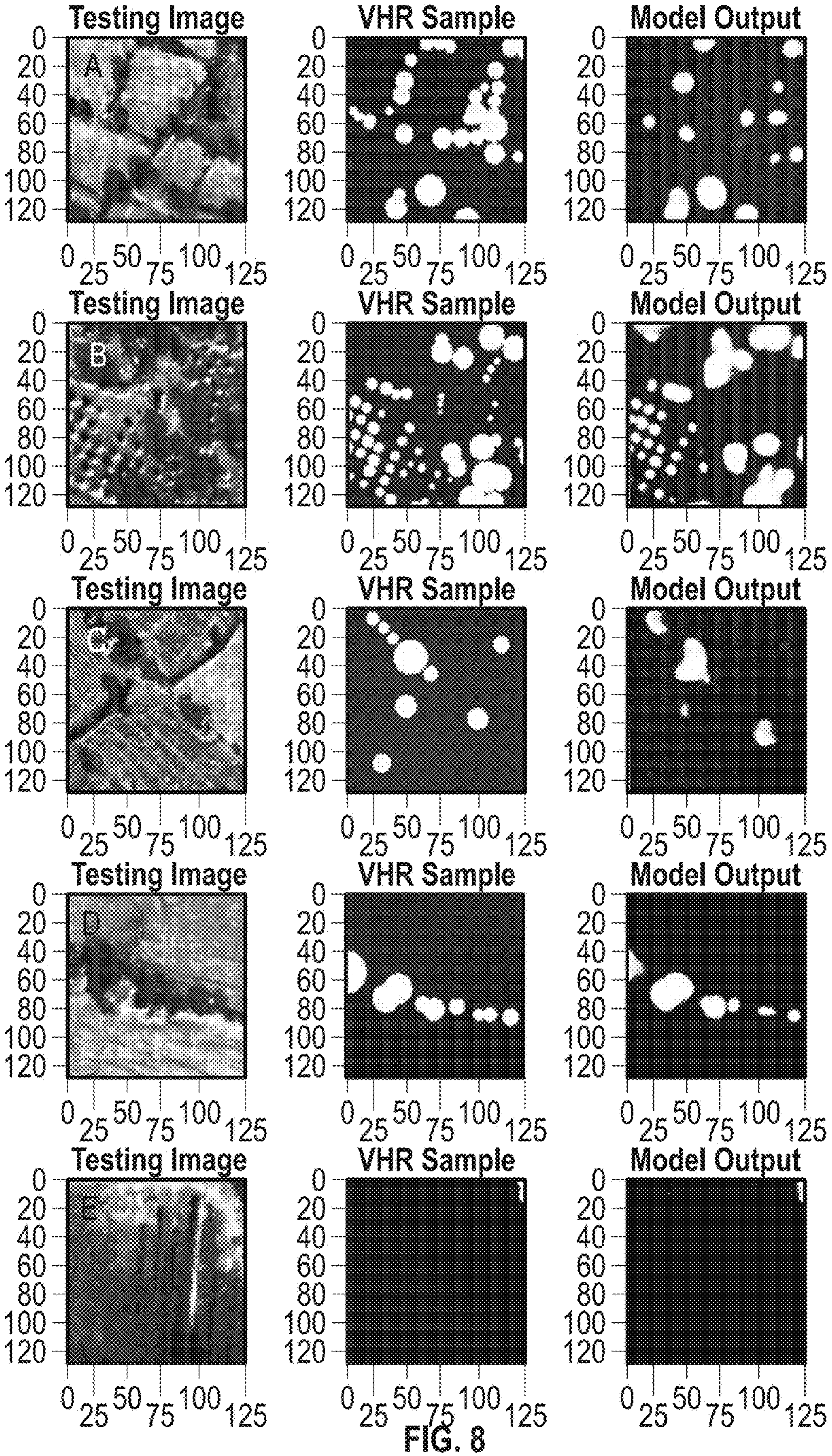
FIG. 8 are a plurality of plots showing a testing image of very high resolution image and the model output.

Referring now to FIGS. 7A, 7B and 8, accuracy metrics for the VHR deep learning model is set forth. The UNet/ResNet deep learning algorithm is applied to 0.5 m resolution VHR data, generating accuracy metrics. The algorithm produces a model using 404 samples, with 90% used for training and 10% used for validation, with learning stopped after 15 epochs (batch size 6). Metrics are produced internally for Validation Loss, which measures how well predictions match the training labels, and Validation Accuracy, which measures the proportion of correct predictions in the validation set. The model converges on Validation Loss of 0.2 and Accuracy of 0.95 shown in FIGS. 7A and 7B.

FIG. 8 presents a selection of samples, labels and predictions during training and testing. Examples of training and testing samples for the VHR UNet model is set forth. The left-hand column is an example 128×128 pixel samples. The middle column contains the labels. The right-hand column is the model prediction. Examples are in row A: TOF linear hedgerows; Row B: Plantations; Row C: Mixed scattered trees; Row D: Linear trees; and Row E: only shrubs or saplings.

Figure 9:
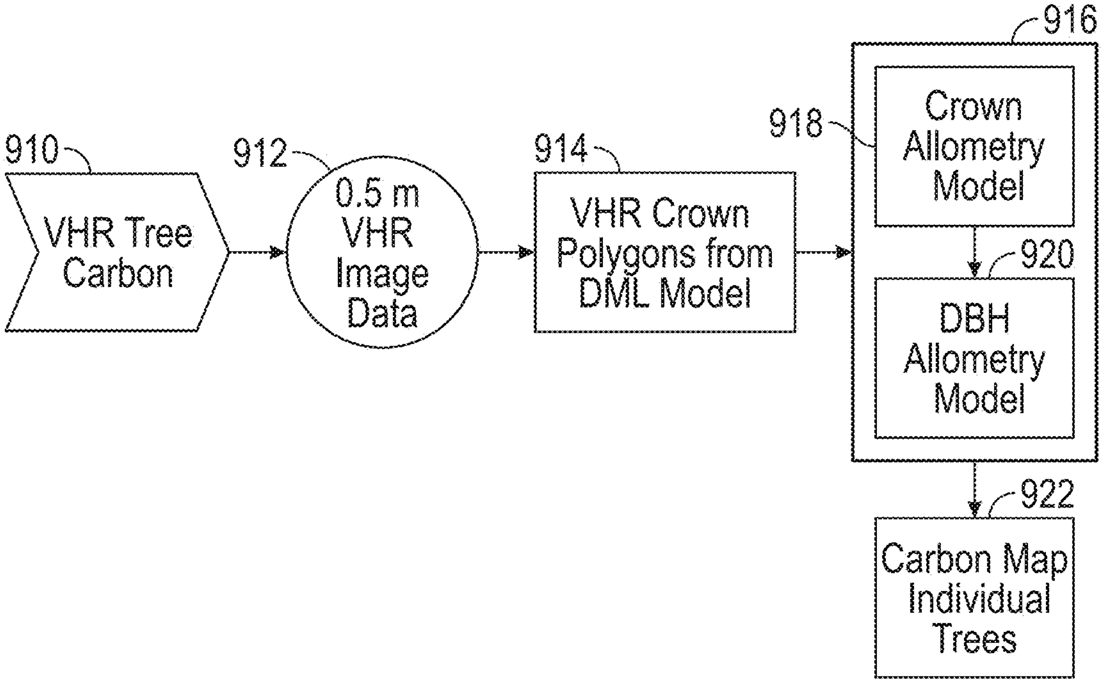
FIG. 9 is a flowchart of a method for determining a carbon map for individual trees.

Referring now to FIG. 9, a method 910 of processing of VHR data for individual tree carbon is based on a conceptual and scientific model that uses allometric scaling of tree parameters to whole tree biomass. In step 912, very high resolution VHR image data Is received, and the crowns are determined therefrom in step 914. In step 914, the VHR data is run through the DML model as described above to map tree crown polygons. Local measurements are used to provide a crown allometry model 916 from the area. The model determines the diameter at breast heigh (DBH) using crown allometry in model 920. In step 922 the carbon for each tree may be determined. That is, carbon based on a crown-based estimation of tree stem diameter which, in turn, applies an individual tree allometric scaling model based on stem diameter at breast height, the carbon for each tree may be determined and mapped.

The preparation of high-resolution TOF maps at the individual tree crown level enables the preparation of individual tree carbon maps across very large landscapes and geographic areas in step 922. The advantage of an individual tree crown map is that allometric scaling can be appropriately used to estimate biomass and carbon as mentioned earlier. Many remote sensing approaches are limited to biomass mapping of tree cover with data that are so coarse that generalized tree canopy cover forms the basis of biomass estimation. Allometric scaling requires using individual tree structural parameters. Moreover, using individual tree parameters, such as stem diameter, there is a wide range of allometric models (equations) available which can then account for landscape or tree-type-specific differences. Even with canopy cover models calibrated against sample plot data often no finer resolution than 50 m, nonlinearities can introduce errors. However, most allometric equations are based on tree stem diameter or tree height and when using the height structural parameter, the stem diameter is also required. This presents a problem for remote sensing because stem diameter cannot be directly measured with satellites.

Allometric scaling of tree carbon is performed in the present system. The Natsure.ai system 10 produces a novel method for allometric scaling in which ground calibration is used to estimate stem diameters from tree crown dimensions. Individual tree crown projected area (CPA) is the primary output of our VHR data machine learning model described above in step 914. The deep learning model segments pixels representing tree crowns, which are then vectorized to generate tree crown polygons, from which are used to compute the crown projected area (CPA) as well as other crown dimensions as set forth in FIG. 3A. This deploys a processing stream method that uses sample-based ground measurement of stem diameter and crown projected area. The sampling scheme is based on model landscapes covering approximately 5,468 $km^2$ where field measurements are deployed.

The processing of VHR data proceeds with inputs from the DML model which produced the tree crown polygons. Field level data calibrate two allometry models to make the per-tree carbon attributes.

Within each model landscape to obtain the crown allometry model 918 and DBH allometry model 920, 10 sites were identified, each measuring 10 km×10 km. At each site, a random selection of five (5) 1 ha fixed radius circular sample areas of interest 330 were established. The number of sample plots was determined by an a priori estimation of the required number of plots needed to acquire measurements on more than 500 trees; for this study 1,180 trees for stem diameters at breast height (DBH) and crown projected area (CPA) were measured. Ground measured CPA was based on two radial canopy diameter measurements, using the longest canopy axis and its perpendicular axis. On the ground, individual trees in field-ready imagery were identified and simultaneously matched, and geo-tagged each tree with field GPS. The allometric parameters are completely disaggregated and matched tree-by-tree in the database. Also, tree height, tree location, species type, landscape descriptions and geotagged photos were collected. Using ground collected allometric measurements an ordinary least squares linear regression was estimated from the independent variable of CPA and a dependent estimate of DBH. This produced a simple model to estimate DBH from remote sensing CPA which we retrieve for each tree in the landscape test area from the VHR machine-learning model product. The aim of estimating DBH from remote sensing, rather than directly estimating carbon, is to make the approach compatible with national forest inventory practices in India that routinely use existing allometric equations. The remote sensing produced a map of CPA for all trees in the landscape, from which each tree's DBH was estimated from the regression model.

Figure 10:
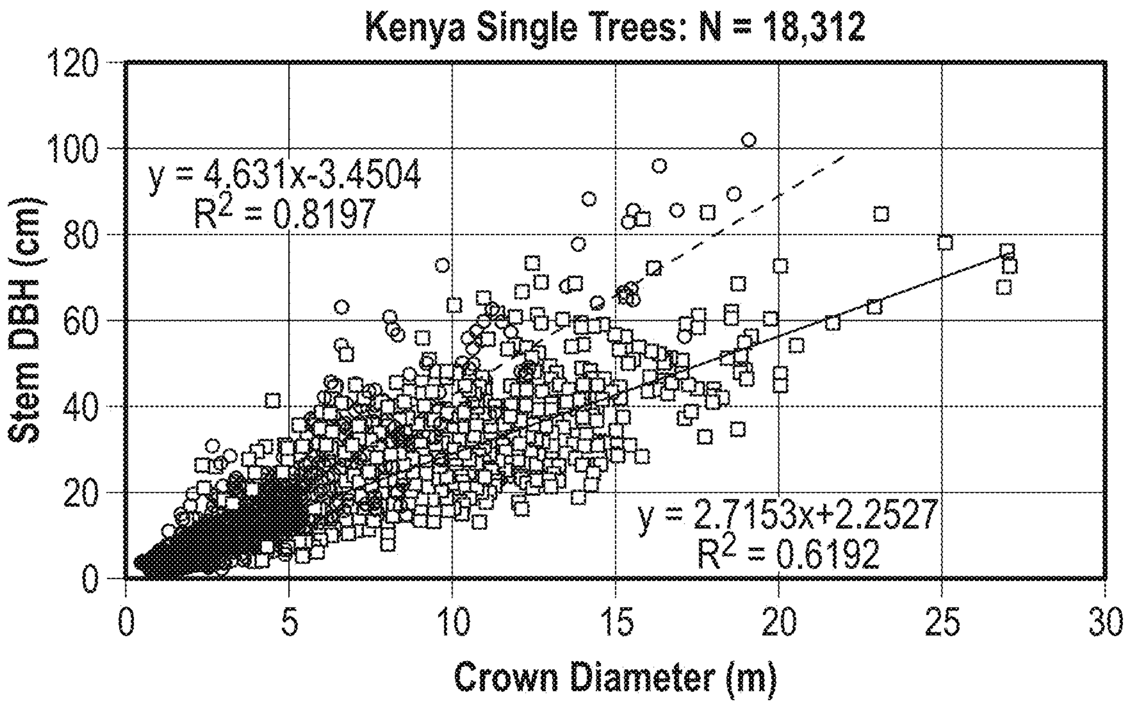
FIG. 10 are plots for the relationship diameter at rest height versus crown diameter for trees in an area.

There are two libraries of allometric models, represented as equations, that are used in this analysis. The first is a series of allometric calibration equations which relate tree crown area or diameter, represented as the Crown Projected Area (CPA) or Crown Diameter (CD) to its stem diameter, represented as the Diameter at Breast Height (DBH) which is conventionally 1.3 m above the base of a tree trunk. These relationships are derived from a protocol for field data collection, which is described in detail in Module 3. The second is a series of allometric scaling equations which relates the stem DBH to the total tree above ground biomass, which get converted to carbon. These relationships are also derived from a protocol for field data collection. An example of the allometric calibration is shown in FIG. 10 from Kenya.

Referring now to FIGS. 11A and 11B, allometric calibration models for estimating diameter at breast height (DBH) is illustrated. In FIG. 11B, equations for determining above ground biomass based on DBH is set forth.

Figure 12:
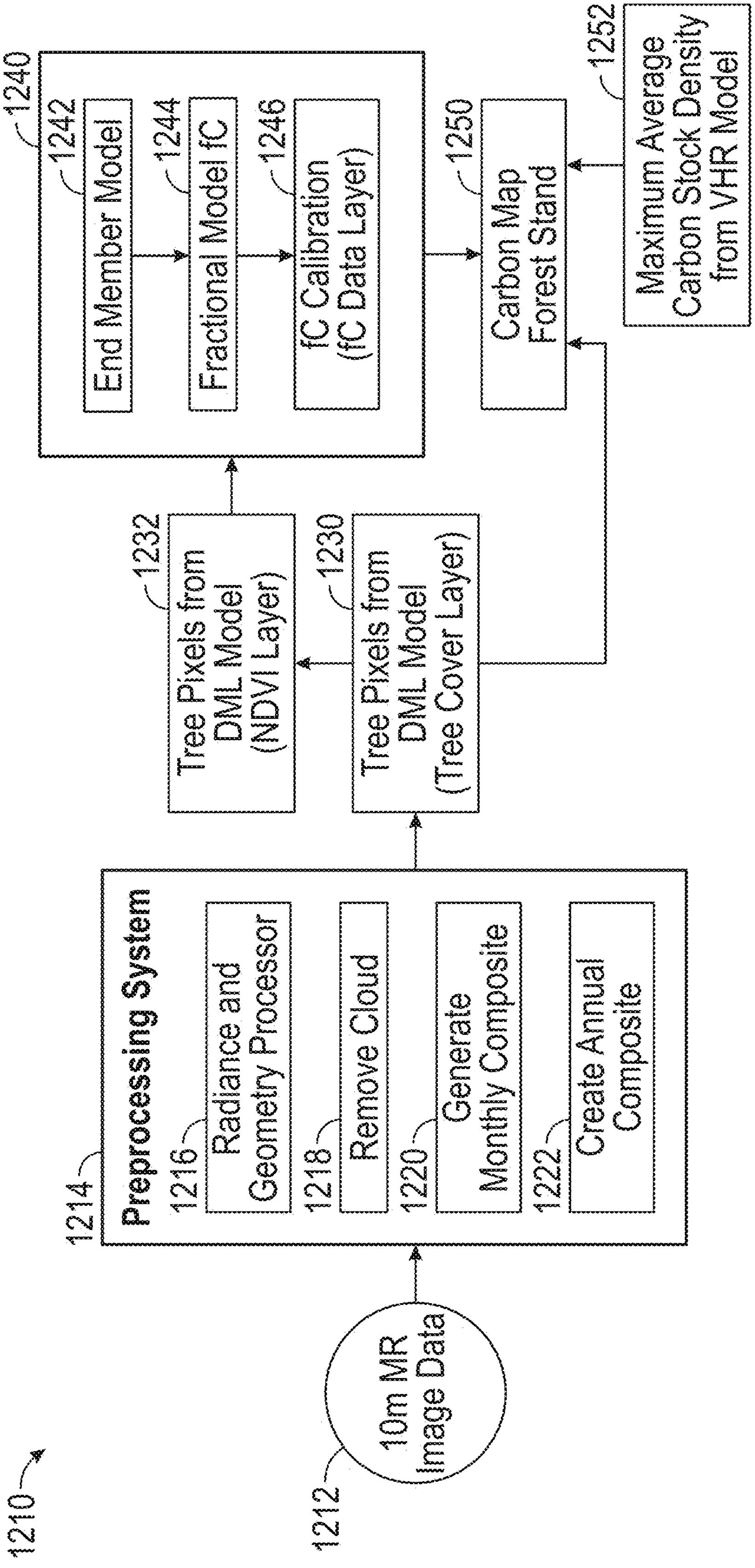
FIG. 12 is a flowchart of a method for generating a carbon map for a forest stand.

Referring now to FIG. 12 a detailed process for determining moderate forest stand carbon in 1210 is set forth. The processing of 10 m moderate resolution (MR) data follows the processing method for VHR data in most respects. There are minor differences in the pre-processing related to compositing, and major differences in the attribution of biomass and carbon to the satellite data products. These differences are described here. The core modeling using the DML methods is the same for 10 m data as 0.5 m data.

The pre-processing of 10 m MR data follows the same steps for geometric correction, rectification, atmospheric correction, and cloud removal. Following this basic processing the Natsure.ai system takes advantage of the availability of a large number of images with repeat coverage in a single year. This allows for use of optimal selection of quality pixels, with cloud and cloud shadows removed and other atmospheric factors corrected.

Unlike the VHR data, the MR data needs to be composited because the source dataset consists of several images acquired on a near daily basis over the course of a year, providing a very dense time series. The compositing process involves selection of the best cloud free pixels from several individual images in each month, and then creating a single monthly layer of the average acquisition digital number or NDVI index for each month of the year as illustrated above in FIG. 4.

The composite MR dataset, with 3-band monthly layers is obtained in step 1212 and is used as input layers to the DML processing framework to produce an output layer with individual tree cover at the 10 m resolution. Unblike with the VHR data, this output layer is mapping all "hot" MR pixels. That is where individual tree cover is detected, but actual crown cover is not able to be measured since an entire MR pixel is identified.

To quantify carbon, another MR data layer is produced, based on a measure of fractional cover (fC), and merged with the tree detection layer in FIG. 12. The measure of fC is between 0.0 and 1.0 and represents the quantitative fraction of green vegetation in the MR detected pixel. So, to further process the carbon the fC values are calibrated in step 1246 against a calibration dataset in which the VHR carbon has been mapped. The regression between the VHR-mapped carbon and the fC value in detected pixels is the model 1244 for carbon estimation. This model is used to down-calibrate a maximum carbon value which is pre-determined in advance, from field data as described below and VHR carbon estimation as described above.

More specially, analysis-ready data is generated from moderate resolution data (MR) data in three steps. The pre-processing system 1214 performs a series of steps to pre-processed data. Step 1216 pre-processes the data for radiance and geometry. This means corrections may be made to the raw sensor data to correct for distortions such as atmospheric distortions and geometric distortions or inconsistencies. Step 1218 removes clouds. Step 1220 produces monthly composites. The process creates cloud-free mosaics of MR imagery for a given year in step 1222. To generate cloud-free data, images are selected based on the least cloudy image for all images in a year, with at least one image with less than 30% cloud cover. Clouds and cloud shadow masks are generated for each of the selected images. These masks are used to generate cloud-free individual images. The complete image collection is split into calendar months and each month's median value was computed for all visible and near-infra-red (VNIR) spectral bands, cloud-free, monthly data are produced by gap-filling with images from the previous and subsequent months. Remaining cloud or cloud shadow gaps in the monthly products are filled these by interpolating between the images of the previous and next months where cloud-free data existed. This produces composite input layers: three near-infrared (NIR) bands for each of 12 months. The input layers of pre-processed data are used with the DML model to map pixels in which tree cover layers (tree pixels) are detected in step 1230.

Deep learning algorithms are employed to map tree cover outside of forests in large landscapes. To develop the model, a residual neural network (ResNet50) can be used. Other model frameworks can be used including segmentation and transformers. The model architecture processes 64-meter× 64-meter VHR images with a resolution of 0.5 meters. In this example, the training was conducted on an AMD 20 GPU provided by Michigan State University's High-Performance Computing Clusters.

Training samples, each consisting of 512×512 pixel blocks, were generated and the target labels are derived from manual and overlay of the 10 m grid over VHR tree canopy data which is merged with the 10 m MR data. In one instantiation of the model, these training data are used with a deep neural network-based framework based on U-Net architecture. U-Net is a fully convolutional network. The network consists of a contracting path and an expansive path, which gives it the U-shaped architecture. U-Net consists of an encoder for down-sampling and a decoder for up-sampling with skip connections. In this case, the resulting model contains 31,110,497 trainable parameters. The model used for training was a U-Net deep neural network, characterized by an encoder-decoder architecture with skip connections. The encoder employs convolutional and pooling layers to capture hierarchical features through down-sampling, while the decoder up-sampled these features to produce segmented outputs.

Classification of "hot" pixels, indicating significant tree cover, is determined using a 40% probability threshold. Predictions were further aggregated into 70 m×70 m mapping blocks (0.49 hectares). Blocks with more than 70% tree cover pixels (equivalent to more than 35 pixels) are classified as forested areas, while others as classified as tree cover outside of forests (TOF). This methodology ensures precise differentiation between forested and non-forested areas, leveraging detailed pixel-level predictions and block-level aggregation.

The deep machine learning (DML) model produces a tree map but does not map carbon. To provide an estimation of carbon, the framework uses the pre-processed composited MR data layers to produce a normalized difference vegetative index (NDVI) layer in step 1232. This NDVI layer is used to produce a fractional cover (fC) layer from the input NDVI layer in step 1240 using spectral unmixing methods and linear end member analysis.

A vegetation continuous-field, fractional cover (fC) product is produced from the NDVI data using a two end member, linear un-mixing algorithm. This product is adjusted by masking pixels of no-data, that is, using only the detected pixels form the DML model. The process uses constants and radiometric calibration procedure for each sensor provided in literature. This pre-requisite step of radiometric characterization and calibration is known to produce higher quality "down-stream" products, by reducing errors in observed Earth surface changes from sensor artifacts when using long-term series of remote sensing data for scientific information. Conversion to TOA reflectance uses scene specific data related to the date of acquisition and position relative to the sun's position at the time of acquisition. The conversion from digital numbers (DNs) data to at-sensor spectral radiance and then to TOA reflectance is done for each spectral band for each acquired image.

The Normalized Difference Vegetation Index (NDVI) layer of step 1232 is created using the NIR and Red top-of-atmosphere (TOA) reflectance bands. The NDVI layer is a measure of vegetation across the landscape with values between 0 and 1. NDVI pixel values closer to one contain vegetation with high photosynthetic capacity. The equation for NDVI is (NIR−Red)/(NIR+RED).

Vegetation continuous field fractional cover (fC) data layer is generated from the NDVI data using a two end-member, linear un-mixing model. The model 1242 uses two end members representing pure soil (VIsoil) and 100% closed canopy vegetation (VIforest). The end-members are selected using an automated optical inspection (AOI) tool through expert knowledge visual analysis for each Landsat NDVI image or along-path mosaic paired with a histogram stretched RGB three-band false-color composite image. Several AOI samples are selected for each end-member throughout an image. The minimum, maximum, mean, and standard deviation are computed from the AOI end-member samples. Along path (same date) and individual scene fC products are created using the minimum, maximum and average end-member values and each are evaluated for path-to-path and gap-filling consistency prior to selection for mosaicking and gap-filling. The fC data are produced as thematic integers and scaled 0 to 100. The fC algorithm is specified as follows: (NDVI−VIsoil)/(VIforest−VIsoil).

The fC data layer can be merged with the DML detected tree layer to estimate carbon in step 1250. The first step is to determine from the DML VHR Model a maximum average carbon stock density for the landscape area of interest in step 1252. This can be done through sampling as described above. The maximum carbon stock of a 10 m pixel can be estimated and used to down-calibrate based on the relationship between fC and carbon as part of step 1250. This relationship is determined using ordinary regression.

Figure 13:
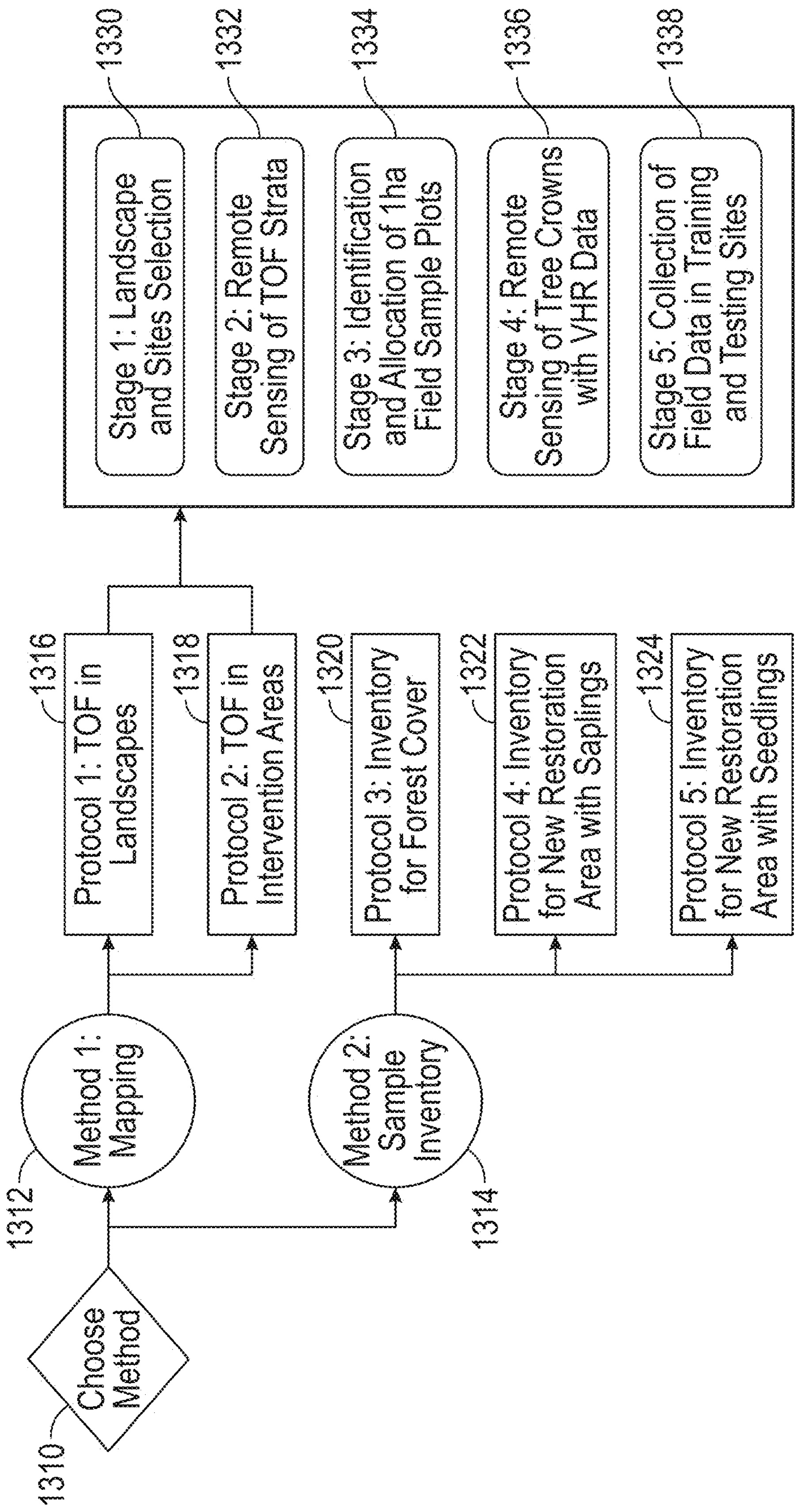
FIG. 13 is a flowchart of a method for performing mapping and sampling an inventory.

Referring now to FIG. 13, methods for carbon estimation on project sites and landscapes are set forth. Landscapes vary relative to the types of vegetation for a certain area including the types of trees and the amount of the different types. This work is structured into two methods, one for field reconnaissance and the second for field deployment. Field measurement deployment protocols are further organized into two general methods and five associated protocols.

The process begins in FIG. 1310 which allows a choice between a first method and a second method. The first method for field reconnaissance may be referred to as a "Windshield Survey" and begins in step 1312 where the team inspects the landscape and gathers observations that inform the analysis and field measurement itself. The field reconnaissance is meant to gather information to develop a broad measurement plan or framework for the projects within a portfolio of projects. As such it is done on a small cross sectional sample of projects within the portfolio. To do this, an initial assessment of the project portfolio is made through a formal process to inventory and define various characteristics of projects within the portfolio.

During the field reconnaissance effort, detailed photographic and documentary information is compiled about the site where restoration is taking place, the ecological context, and what types of interventions are occurring. It defines the context and uses very high-resolution satellite data as the map base for notation and commentary.

In step 1314, the second method for field deployment is actual measurements using sample plots in which parameters that relate tree characteristics, usually allometric scaling parameters, to tree and stand biomass are measured. These characteristics can then be transformed into tree or tree-cover carbon stocks.

The first part method is based on mapping, in which field measurements are gathered as input for a model that interrelates allometric parameters from the field with remote sensing. Crown Projected Area (CPA) and Diameter at Breast Height (DBH) are collected in the field in random 1 ha circular plots, and a relationship between the two characteristics is calculated. In parallel, very-high-resolution imagery of the sample plot area is acquired, and individual tree crowns are mapped using machine learning image segmentation analysis. Measures of DBH obtained from field measurements are then specifically associated with individual trees and their mapped CPAs. This, in turn, allows the use of a standard allometric equation based on DBH to compute individual tree carbon stocks from CPA. This mapping is then applied to very high-resolution remote sensing data to map carbon in large landscapes at the tree level.

The second method is based on a sample Inventory, in which measurements are used to directly estimate the carbon stock of tree cover in sites with seedlings, saplings, or continuous tree cover that cannot be delineated in the mapping approach. This method uses standard forest inventory methods to sample a limited area or whole forest stand. Depending on the nature of the sample plot arrangements (clustered or non-clustered plots) the plot estimates are averaged and then extrapolated using an expansion factor to the entire project or stand area, either in total or by strata. This biomass is converted to carbon stocks using a standard conversion factor (C=0.5*Biomass).

Within the two Methods are five Protocols for field data collection. Under the mapping method are two detailed protocols for how to collect data for trees outside of forests (TOF) in landscapes in step 1316 and intervention areas including planted trees, isolated trees, plantations and agroforestry and other individual tree-based activities in step 1318.

Both protocols 1 in step 1316 and protocol 2 in step 1318 have five associated stages of field data collection.

Generally, Method 1 (Mapping) will be the primary method for estimating carbon on project sites and in landscapes, and Method 2 (Inventory) will be used to add additional detail at the discretion of the MSU team for project sites with seedlings, saplings, or continuous tree cover that cannot be measured in the mapping approach. The mapping method in step 1312 is based on remote sensing and is used to measure carbon stocks in individual trees with detectable tree canopies (greater than 5 m2), for the entire landscape using a "wall-to-wall" approach, which measures and reports continuously across the entire landscape (not based on a sample frame). The mapping method also reports for trees within sites where trees are present in the baseline and at months 72 and 120. The mapping method does require field sampling to collect data for its crown-based allometric scaling of remote sensing measurement and delineation of tree crowns.

Under the second (inventory) method there are three protocols depending on what type of site or intervention is being measured. These are whole stands of forest or continuous tree cover in step 1320, new restoration areas as sites or projects with saplings in step 1322 and new restoration areas as sites or projects with seedlings in step 1324.

In general, the inventory method is supplementally used when: 1) measurements of seedlings and saplings are required, 2) when small trees below the mapping detection limit are found, or for other important layers such as shrubs, 3) when closed canopy forests or woodlands are measured. The inventory method starting in step 1314 is sample based. The sample frame for the inventory method is a statistical sampling of carbon stocks directly, and as such needs to be extrapolated across a land unit represented by the sample. It may require considerable field time and effort, for instance in cases of large areas or dense forest cover.

Soil carbon, and litter will not be included in carbon estimations. Belowground live biomass will not be measured directly, instead a standard root-to-shoot ratio of 0.26 will be used for both methods. Shrubs and standing and lying dead wood will only be measured and included in the sample inventory method starting in step 1314 carbon estimates.

For the first method at step 1312, the first objective of a field deployment will be to document the local tree and vegetation cover context by making observations of field conditions. This will be a driving or on-foot survey of the project, taking note of the overall landscape features and how the project is implementing tree-based activities. Using the camera or phone for photos, locations are marked with GPS and a log of photos is kept and organized by number or order.

First, the field team goes to the project general areas and write notes and photos. Imagery is also consulted and annotated with notes on trees and other objects (e.g. shrubs). This is a ground-truthing effort, which will be used later to interpret the landscape. Then, the field team goes to project sites and take notes and photos. It is not necessary to identify species, but the general type of trees is noted. The objective is to build a map of the area where landscape features can be filtered into those that are natural objects not directly associated with the restoration work and those that are directly a result of the interventions.

The field work objective for the mapping method in step 1316 is to collect a dataset of tree parameters, chiefly diameter at breast height (DBH), Crown Projected Area (CPA) and Crown Diameter, for developing an allometric model. The data collection protocol involves five stages 1330-1338:

In the first stage 1330 conducting a landscape selection exercise to identify large landscapes to do the work is performed. This stage is limited to the selection of sampling locations for developing the allometric relationship between field measured DBH and CPA or Crown Diameter.

In the second stage 1332 remote sensing mapping of areas (strata) of TOF at a broad scale and resolution using Landsat or Sentinel-2 data (predominantly Sentinel-2) is performed.

In the third stage 1334, identification of a large sample of 1 ha plots for measurement of tree allometric parameters in areas of high density TOF, using the spatial characteristics and crown size characteristics from the remote sensing to guide sample locations and sample allocation is performed.

In the fourth stage 1336, remote sensing of training sites and testing sites using very high resolution (VHR) remote sensing data from Worldview/MAXAR (35 cm resolution) to create a machine learning model. Generalized models which may be used in several countries are developed.

In the fifth stage 1338, machine learning model across the landscape at <1 m resolution to map tree crowns and then using the CPA-to-DBH allometry to assign carbon stocks is performed.

The reporting product is a map of carbon estimates predicted for individual trees delineated in VHR imagery, resulting in a per-tree carbon map for project sites and landscapes.

In stage 1 in step 1330, landscapes are sometimes pre-identified, so this stage can be limited to the selection and allocation of training and testing sites. Ten training sites and ten testing sites, each about 4 km2 in area, are identified randomly within each project's landscape. Inside the training and testing sites, a set number of 1 ha plots for ground data collection, as described in stage 3 are employed.

In stage 2 remote sensing of TOF strata is determined in step 1332. Using Sentinel data, the deployment of a map of TOF cover at the 10 m resolution is performed. The data shall be used to define the TOF strata, if needed. The TOF strata is the estimated cover area of trees outside forests. It is used for locating additional training and test sites, each being 4 km2 in area.

In stage 3 identification and allocation of 1 ha field sample plots is performed in step 1334. For stage 3 in step 1334 two options are identified, depending on scope and available resources. The first uses the machine learning training and testing sites. The second uses only a purposeful selection of sample plots in the landscape. Within each training and testing site, the team identifies the centroid of 10 random 1 ha circular plots. For the selection of purposeful sample plots the team selects enough sample plots to obtain approximately 100-200 trees per landscape. The team will ensure that some of the 1 ha plots are located inside project landscapes and/or sites.

A follow-up step in plot allocation is related to "modulating" the sample allocation to accommodate the VHR remote sensing analysis. This is discussed below in Stage 4, step 1336, and is an adjustment to the plot allocation to ensure there is a representative distribution of tree sizes and other factors important to the development of the model.

This shall reduce statistical outliers and in principle make the model more tailored to the mapping feature object (crown area).

In stage 4 at step 1336 remote sensing of tree crowns with VHR Data is performed. Individual tree crowns are mapped on VHR imagery within each training and testing site, as well as in the larger landscape. This shall be the first deployment of one of the output products from the work but will also provide the basis for field data collection. Using maps of CPAs from VHR remote sensing data, the field team will ensure that there is a direct match between the trees in the sample plots and the same trees identified in the VHR data. This is important because the variables in the regression model are the tree stem DBH in the field and their precise counterpart CPA from the remote sensing. Similarly for consistency checking later, field measurements of CPA will be collected to be associated with the same tree in the VHR data map of CPA.

The remote sensing adds important information in the sample plots allocation such as information on the size-class distribution of CPAs. To ensure that the plot allocation captures a robust distribution of CPAs across all size classes, a modulation of the allocation is made to ensure the CPA distribution is proportional to the landscape distribution. Thus, some plots are either removed or added.

In stage 5, step 1338, collection of field data in training and testing sites is performed. Field data collection in the mapping method of step 1312 is compared to the inventory method of step 1314. The purpose of this stage of the method is to collect data for building the machine learning crown mapping model and the crown-based allometric scaling model, not area-representative sampling of actual biomass by tree carbon measurements, as in the inventory method.

Therefore, although it is useful to have 1 ha plots delineated precisely in the field, it does not actually impact the model development if there are minor imprecisions in the delineation of the plot boundaries. All reasonable effort should be made to work within a 1 ha plot, but where boundaries are uncertain, this will be noted in field notes.

Each allocated sample plot is located in the field using the plot centroid and GPS, and a fixed radius of 56.42 m for a 1 ha circular plot is measured. The following measurements are taken and identified precisely in the VHR remote sensing map including plot number and plot features notes, date, tree locations, GPS and identified on VHR map, a tree identification number having a tree identifier and plot identifier, all identified on the VHR map, a tree species name, DBH (cm), CPA (m) measured using the long axis crown diameter and a perpendicular diameter, and tree height.

At each 1 ha plot, start with the tree nearest to due North and begin a clockwise sampling of individual trees, marking the GPS location and marking on a paper or digital map the tree identification. Take photos in cardinal directions, starting due North and rotating clockwise. Copious field notes are taken at each plot, including a labelling of all measured trees on paper and on the corresponding VHR imagery. These field data are the basis for developing an allometric scaling model using crown dimensions instead of stem or other tree dimensions. This is because remote sensing detects only objects it can image from the satellite instrument in orbit. In this case the dimension is the crown projected area, crown diameter, or related crown measures. This allometric scaling model is a regression between field collected crown data and field collected stem diameters. The crown measurements are made using the remote sensing machine learning model. They are represented in spatial format in a GIS as polygons of crown areas. The crown based allometric scaling model predicts a tree's diameter from its crown dimensions. Thus, for each mapped tree the predicted stem diameter is sed with a standard allometric equation for the region, landscape, or vegetation cover type. This approach thus allows for use of a variety of local equations and for new equations to be used later.

To compute carbon from the predicted stem diameters the team shall use the allometric equations.

Method 2 inventory through a plot sample frame and protocols 3, 4, 5 is described in greater detail in steps 1320-1324.

Referring now also to FIG. 14 for sites with continuous forest cover, recently planted saplings or seedlings, an additional sample Inventory will be conducted. This method uses standard forest inventory methods to sample a limited area or forest stand, which is then used to estimate select carbon pools in the project site in FIG. 14. Carbon estimates from this inventory will be added to the carbon map.

Figure 15A:
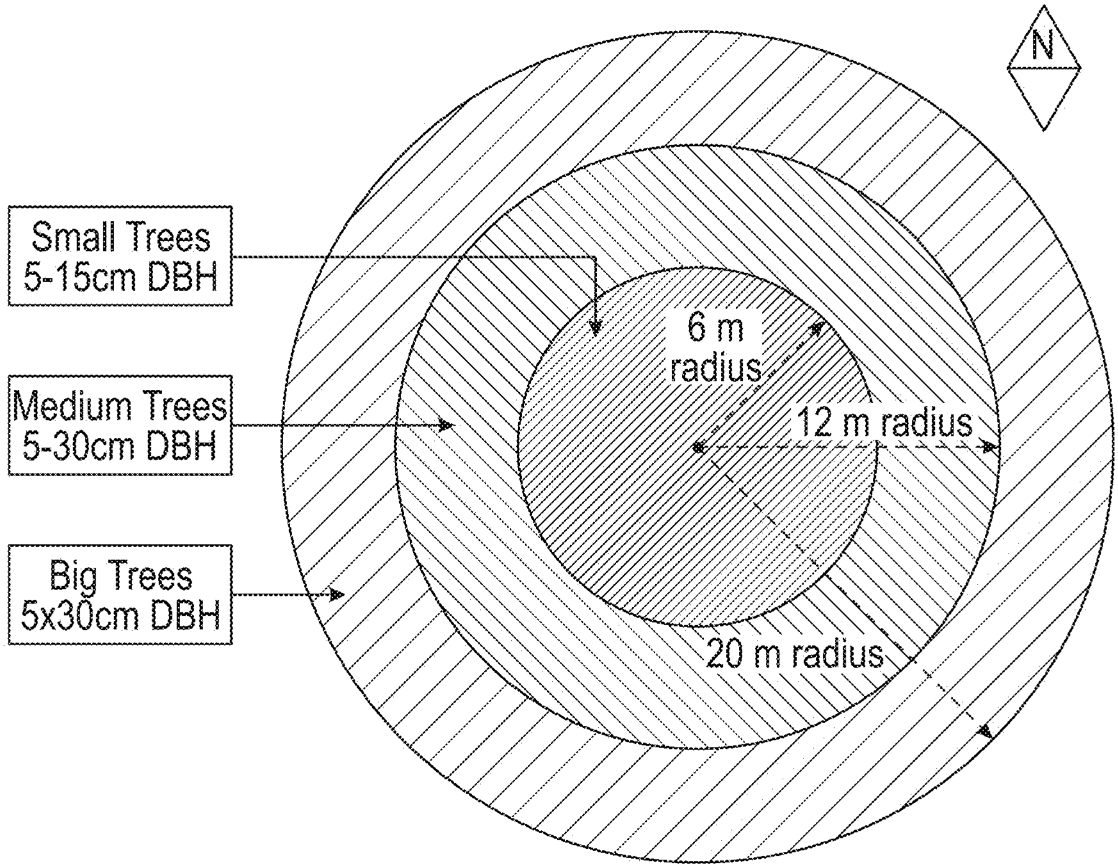
FIG. 15A is a diagram showing the relationship of the crown radius versus the diameter at breast height.

Referring now to FIG. 15A, plot designs for tree inventory is created. The selection of sample trees will be done in fixed size circular plots, which are easy to establish in the field and can be demarcated with simple tools and procedures. The sampling point design applied in the field inventory follows this scheme for a nest plots design to capture both large and small trees for 6 m Radius Circular Plot—small trees 5-15 cm DBH; 12 m Radius Circular Plot—medium trees 15-30 cm DBH, and 20 m Radius Circular Plot—big trees >30 cm DBH.Tree Measurement The following tree characteristics will be measured an assessed in each sample plot to estimate forest biomass (and timber volume): Genus—all trees; Species—all trees; Diameter at breast height (DBH)—all trees; Canopy height—all trees >15 cm DBH (only at the primary plot); and Canopy projected area (CPA)—all trees >15 cm DBH (only at the primary plot).

Figure 15B:
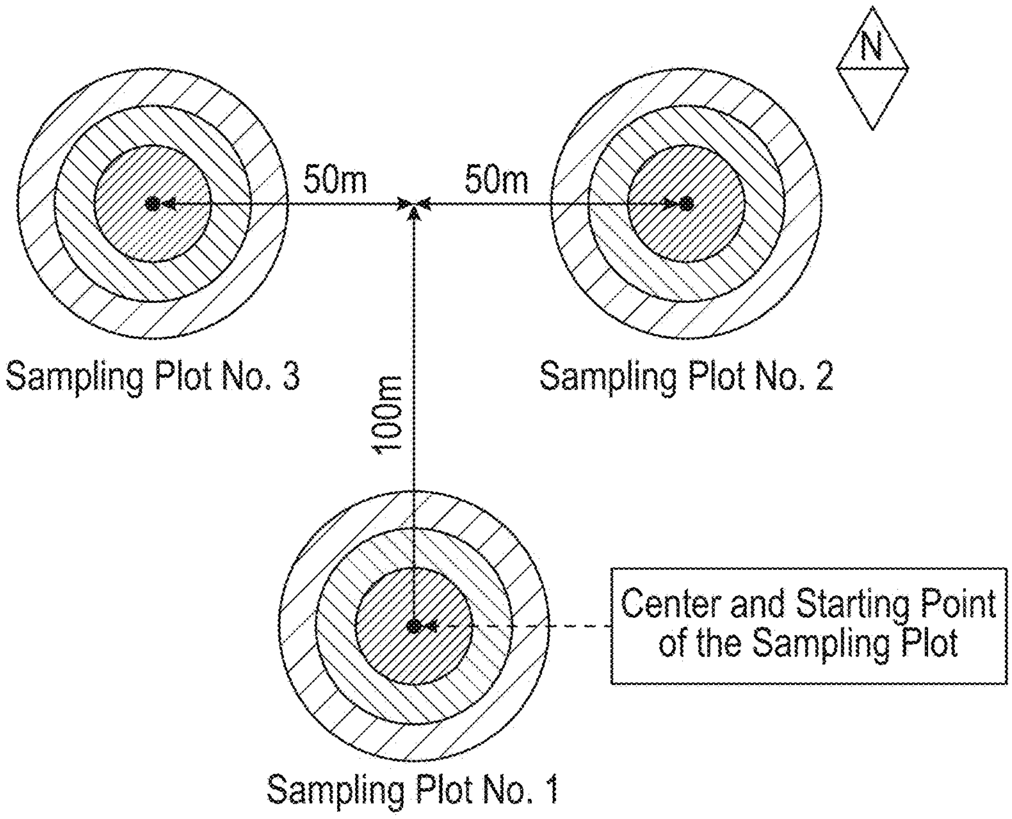
FIG. 15B shows a plot and the relationship to various trees.

In FIG. 15B standing dead wood is estimated by assigning dead trees into two classes based on their decomposition—dead trees with branches still attached to stem or dead trees without any branches remaining on the stem. For standing dead trees without branches attached to the trunk, estimate stem volume, and calculate biomass by multiplying with the correct density class for dead wood (sound, intermediate, rotten). The stem volume is calculated by measuring the DHB.

Figure 15C:
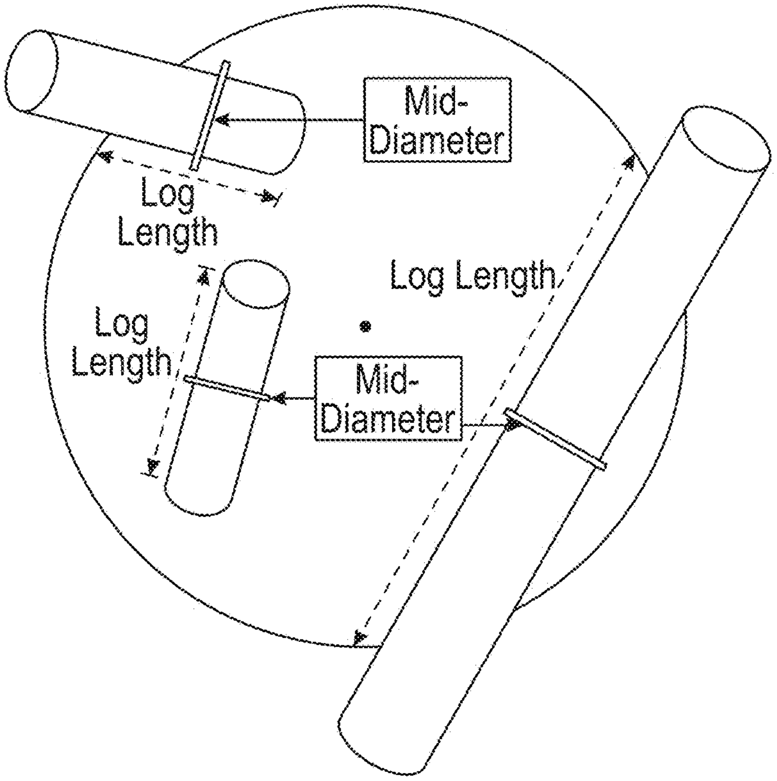
FIG. 15C shows a representative layout for dead wood.

Lying dead wood measured inside the largest nested plot using the scheme shown in FIG. 15C. Measure the diameter (cm) of all lying dead wood >15 cm and calculate the volume using the appropriate formula. Record the decay class for each piece of lying dead wood. Determine biomass by applying the wood density class for each piece of lying dead wood.

Additional technical details about the field measurement protocol can be found in the MSU Standard Operating Procedures (Standard Operating Procedures: Forest Carbon Inventory, Data Collection and Reporting: Volumes 1 and 2), the disclosure of which is incorporated by reference herein.

Above ground biomass (AGB) estimates generated by the sample inventory focus on trees as the dominant component of the AGB pool. Most of the components of AGB are not directly measured through destructive sampling but are typically estimated by genus or species-specific volume equations (converted to mass by means of density) or by allometric equations that directly predict the AGB. Although there are many allometric equations available for temperate zone species, many tropical tree species do not have a species-specific allometric equation. Field teams can select among several general equations for the appropriate landscape, target land use type, or ecosystem type but these equations should be verified to be accurate for the project location.

In method 2, protocol 3, step 1320 inventory for forest cover is performed. For forested parts of the project site's landscape (area greater than a half-hectare that has at least 10% canopy cover and is not being utilized for any other land-use), an additional sample inventory will be completed when it is part of the target land use. Carbon estimates from this inventory will be added to the carbon map created with Method 1, steps 1312-1338 for areas with continuous tree cover that could not be delineated with the mapping Method.

For method 2, protocol 4, step 1322 inventory of new restoration areas with saplings is performed. for parts of the project site where sapling planting has been completed, an additional sample inventory will be completed. Carbon estimates from this inventory will be added to the carbon map created with method 1, steps 1312-1338 for areas with continuous tree cover that could not be delineated with the mapping method 1.

The same methods as Protocol 3, step 1320 will be used but substituting a fixed radius plot of smaller size of 2-10 m as appropriate for the size of the site. Here first count all tree saplings in the plot with a height less than 35 cm. For trees with DBH between 5-10 cm make measurements of the DBH and height. Do not measure dead wood or shrubs or seedlings. The number of plots for this survey is minimal and should be determined based on available time.

An alternative approach is to use a transect method. Here a 6 m wide transect is established in restoration areas with saplings. For saplings great than 30 cm in height, the height and individual count is made and reported. The area of the transect is estimated and the estimates are extrapolated to the size of the Restoration Area. If a standard measure of biomass and height is available the height estimates can be directly translated to biomass per sapling, averaged per hectare and then extrapolated. If there are no standard values of sapling height-based biomass, then either assign a logical estimate or take a destructive sample by harvesting a sample of 30 or more, and getting an estimated biomass per sapling.

In method 2, protocol 5, step 1324 inventory of new restoration areas with seedlings is set forth. Sites with seedlings should be assessed only for planting rates by counting all the individuals in a fixed radius plot of 2-10 m as appropriate. The number of plots sampled should take into account time and effort availability. An alternative is to use a transect method as for saplings, but only providing counts.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

In this application, including the definitions below, the term "module," "network" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method comprising:

receiving at a satellite, reflected light from an object;

forming high resolution satellite image data at the satellite with at least 3 meter resolution;

receiving moderate resolution image data of a landscape area comprising a plurality of pixels, said moderate resolution image data having a resolution lower than the high resolution satellite image data;

processing field collected data and the moderate resolution image data to obtain tree-crown based allometry;

communicating the high resolution satellite image data to a pre-processing system;

pre-processing the high resolution satellite image data to form pre-processed data;

training a trained classifier with the tree-crown based allometry;

communicating the pre-processed data to the trained classifier and deep learning segmentation;

determining at the trained classifier and deep learning segmentation a crown projected area for individual trees;

determining a stem size of each tree using the crown projected area;

determining a carbon stock for each of the individual trees at a processing system using the stem size and the crown projected area; and determining a carbon map for the individual trees.

2. The method of claim 1 wherein the high resolution satellite image data comprises at least a 0.35 meter resolution.

3. The method of claim 1 wherein the high resolution satellite image data comprises at least 0.5 m to 10 m resolution.

4. The method of claim 1 wherein the high resolution satellite image data comprises three or more spectral bands.

5. The method of claim 1 wherein pre-processing comprises pre-processing for radiance.

6. The method of claim 1 wherein pre-processing comprises pre-processing for geometry distortions.

7. A system comprising:

a pre-processing system;

a satellite system in communication with the pre-processing system and forming high resolution satellite image data reflected light from an object with at least 1 meter resolution and communicating the high resolution satellite image data to the pre-processing system, the satellite system forming moderate resolution image data of a landscape area comprising a plurality of pixels, said moderate resolution image data having a resolution lower than the high resolution satellite image data;

the pre-processing system pre-processing the high resolution satellite image data for radiance and at geometric distortions programmed to form pre-processed data and communicating the pre-processed data to a trained classifier;

a processing system processing field collected data and the moderate resolution image data to obtain tree-crown based allometry;

the trained classifier trained with the tree-crown based allometry and programmed to form a crown projected area for individual trees;

the processing system programmed to determine a stem size of each tree using the crown projected area, determine a carbon stock for each of the individual trees using the stem size and the crown-projected area and determine a carbon map for the individual trees.

8. The system of claim 7 wherein the high resolution satellite image data comprises at least a 0.35 meter resolution.

9. The system of claim 7 wherein the high resolution satellite image data comprises at least 0.5 m to 10 m resolution.

10. The system of claim 7 wherein the high resolution satellite image data comprises three or more spectral bands.

11. A method comprising:

receiving at a satellite, reflected light from an object;

forming high resolution satellite image data at the satellite having at least 0.5m resolution with three or more spectral bands;

receiving moderate resolution image data of a landscape area comprising a plurality of pixels, said moderate resolution image data having a resolution lower than the high resolution satellite image data;

processing field collected data and the moderate resolution image data to obtain tree-crown based allometry;

communicating the high resolution satellite image data to a pre-processing system;

pre-processing the high resolution satellite image data for radiance and geometric distortions to form pre-processed data;

training a trained classifier with the tree-crown based allometry;

communicating the pre-processed data to the trained classifier and deep learning segmentation;

determining at the trained classifier and deep learning segmentation a crown projected area for individual trees;

determining a stem size of each tree using the crown projected area;

determining a carbon stock for each of the individual trees at a processing system using the stem size and the crown projected area; and determining a carbon map for the individual trees.

12. The method of claim 11 wherein the high resolution satellite image data comprises at least a 0.35 meter resolution.

* * * * *